US012623006B2

(12) United States Patent
Okuhara

(10) Patent No.: US 12,623,006 B2
(45) Date of Patent: May 12, 2026

(54) MEDICAL INSTRUMENT

(71) Applicant: TERUMO KABUSHIKI KAISHA, Tokyo (JP)

(72) Inventor: Takashi Okuhara, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1070 days.

(21) Appl. No.: 17/695,282

(22) Filed: Mar. 15, 2022

(65) Prior Publication Data

US 2022/0203000 A1     Jun. 30, 2022

Related U.S. Application Data

(63) Continuation of application No. PCT/JP2020/035074, filed on Sep. 16, 2020.

(30) Foreign Application Priority Data

Sep. 17, 2019     (JP) ................................. 2019-168683

(51) Int. Cl.
*A61L 29/14*          (2006.01)
*A61L 29/08*          (2006.01)
          (Continued)

(52) U.S. Cl.
CPC .............. *A61L 29/14* (2013.01); *A61L 29/085* (2013.01); *A61M 25/0045* (2013.01);
          (Continued)

(58) Field of Classification Search
CPC .............. A61M 25/0045; A61M 25/09; A61M 2025/0046; A61M 2025/09133;
          (Continued)

(56) References Cited

U.S. PATENT DOCUMENTS

2011/0082252 A1*    4/2011    Koschabek ........ C09D 151/003
                                                                524/558
2016/0015869 A1      1/2016    Omata et al.

FOREIGN PATENT DOCUMENTS

CN          105073155 A      11/2015
JP          H0833704 A        2/1996
          (Continued)

OTHER PUBLICATIONS

English-language machine translation of JP 2018-000746 (Year: 2018).*

(Continued)

*Primary Examiner* — James C Goloboy
(74) *Attorney, Agent, or Firm* — Buchanan Ingersoll & Rooney PC

(57)          ABSTRACT

The present disclosure can improve durability (particularly, sliding durability) of a surface lubricating layer while maintaining flexibility of a medical instrument. The medical instrument can include: a base whose surface is partially made of a polyester resin; an intermediate layer formed on at least a part of the surface of the base and containing a (meth)acrylic-modified polyester resin and a polyurethane resin; and a surface lubricating layer formed on an upper part of the intermediate layer and containing a block copolymer having a structural unit (A) derived from a hydrophobic monomer and a structural unit (B) derived from a hydrophilic monomer, in which at least one of the hydrophobic monomer and the hydrophilic monomer has a (meth)acryloyl group.

14 Claims, 5 Drawing Sheets

(51) Int. Cl.
    *A61M 25/00*        (2006.01)
    *A61M 25/09*        (2006.01)
    *C09D 153/00*       (2006.01)
    *C09D 167/02*       (2006.01)

(52) U.S. Cl.
    CPC ........... *A61M 25/09* (2013.01); *C09D 153/00* (2013.01); *C09D 167/02* (2013.01); *A61L 2400/10* (2013.01); *A61L 2420/02* (2013.01); *A61L 2420/08* (2013.01); *A61M 2025/0046* (2013.01); *A61M 2025/09133* (2013.01)

(58) Field of Classification Search
    CPC ... C08F 283/02; C09D 153/00; C09D 167/02; A61L 29/085; A61L 29/14; A61L 31/10; A61L 31/14; A61L 2400/10; A61L 2040/02; A61L 2040/08
    See application file for complete search history.

(56) References Cited

FOREIGN PATENT DOCUMENTS

| | | | |
|---|---|---|---|
| JP | H08157626 | A | 6/1996 |
| JP | H11263819 | A | 9/1999 |
| JP | 2002145971 | A | 5/2002 |
| JP | 2002273834 | A | 9/2002 |
| JP | 2006316169 | A | 11/2006 |
| JP | 2007291546 | A | 11/2007 |
| JP | 2018000746 | A * | 1/2018 |
| WO | WO-2016052133 | A1 * | 4/2016 ............. B32B 27/40 |

OTHER PUBLICATIONS

International Search Report (PCT/ISA/210) with translation and Written Opinion (PCT/ISA/237) mailed on Nov. 2, 2020, by the Japan Patent Office as the International Searching Authority for International Application No. PCT/JP2020/035074. (9 pages).

Office Action (The First Office Action) issued Feb. 3, 2023, by the National Intellectual Property Administration, P. R. China in corresponding Chinese Patent Application No. 202080063421.2 and an English translation of the Office Action. (12 pages).

English Translations of the International Search Report (Form PCT/ISA/210) and the Written Opinion of the International Searching Authority (Form PCT/ISA/237) issued Nov. 2, 2020, by the Japanese Patent Office in corresponding International Application No. PCT/JP2020/035074. (6 pages).

* cited by examiner

TABLE 1

| Polyester resin No. | | 1 | 2 | 3 | 4 | 5 | 6 | 7 | 8 | 9 | 10 | 11 |
|---|---|---|---|---|---|---|---|---|---|---|---|---|
| Polycarboxylic acid component | Terephthalic acid (mol%) | 19 | 0 | 12.5 | 17 | 24 | 0 | 0 | 34 | 26 | 13 | 37.5 |
| | Isophthalic acid (mol%) | 6 | 25 | 12.5 | 8 | 6 | 25 | 25 | 11 | 9 | 7 | 12.5 |
| Polyhydric alcohol component (mol%) | | 25 | 25 | 25 | 25 | 30 | 25 | 25 | 45 | 35 | 20 | 50 |
| (Meth)acrylic modification ratio (mol%) | | 50 | 50 | 50 | 50 | 40 | 50 | 50 | 10 | 30 | 60 | 0 |

FIG. 3

TABLE 2

| | | Composition of (meth)acrylic-modified polyester resin | | | Composition of intermediate layer | | Coefficient of kinetic friction (μk) | Confirmation of coating film on intermediate layer | Confirmation of coating film on surface lubricating layer |
|---|---|---|---|---|---|---|---|---|---|
| | Polyester resin No. | Isophthalic acid content (mol%) | Terephthalic acid content (mol%) | (Meth)acrylic modification ratio (mol%) | Polyester resin (mass%) | Polyurethane resin (mass%) | | | |
| Example 1 | 1 | 6 | 19 | 50 | 70 | 30 | 4.3 | A | A |
| Example 2 | 1 | 6 | 19 | 50 | 50 | 50 | 3.6 | A | A |
| Example 3 | 1 | 6 | 19 | 50 | 30 | 70 | 3.9 | A | A |
| Example 4 | 2 | 25 | 0 | 50 | 50 | 50 | 5.4 | B | B |
| Example 5 | 3 | 12.5 | 12.5 | 50 | 50 | 50 | 5.0 | B | B |
| Example 6 | 4 | 8 | 17 | 50 | 50 | 50 | 4.2 | A | A |
| Example 7 | 5 | 6 | 24 | 40 | 50 | 50 | 3.7 | A | A |
| Example 8 | 6 | 25 | 0 | 50 | 50 | 50 | 5.5 | B | B |
| Example 9 | 7 | 25 | 0 | 50 | 50 | 50 | 5.4 | B | B |
| Example 10 | 8 | 11 | 34 | 10 | 50 | 50 | 5.1 | B | B |
| Example 11 | 9 | 9 | 26 | 30 | 50 | 50 | 4.0 | A | A |
| Example 12 | 10 | 7 | 13 | 60 | 50 | 50 | 3.9 | A | A |
| Comparative Example 1 | 1 | 6 | 19 | 50 | 100 | 0 | 4.2 | C | C |
| Comparative Example 2 | - | - | - | - | 0 | 100 | 4.5 | C | C |
| Comparative Example 3 | MD-2000 | - | - | 0 | 50 | 50 | 21.4 | D | D |
| Comparative Example 4 | KT-8803 | - | - | 0 | 50 | 50 | 16.7 | C | C |
| Comparative Example 5 | 11 | 12.5 | 37.5 | 0 | 50 | 50 | 7.2 | B | C |

FIG. 4

TABLE 3

| | Catheter tube No. | Polyester resin No. | Polyester resin (mass%) | Polyurethane resin (mass%) | Terephthalic acid content (mol%) | Isophthalic acid content (mol%) | (Meth)acrylic modification ratio (mol%) | Elastic modulus (MPa) | Evaluation of sliding resistance increase rate |
|---|---|---|---|---|---|---|---|---|---|
| Comparative Example 6 | Comparative 1 | 1 | 100 | 0 | 19 | 6 | 50 | 1150 | B |
| Example 13 | 1 | 1 | 70 | 30 | 19 | 6 | 50 | 983 | A |
| Example 14 | 2 | 1 | 50 | 50 | 19 | 6 | 50 | 832 | A |
| Example 15 | 3 | 1 | 30 | 70 | 19 | 6 | 50 | 601 | A |
| Comparative Example 7 | Comparative 2 | — | 0 | 100 | — | — | — | 366 | B |

FIG. 5

MEDICAL INSTRUMENT

CROSS-REFERENCES TO RELATED APPLICATIONS

This application is a continuation of International Application No. PCT/JP2020/035074 filed on Sep. 16, 2020, which claims priority to Japanese Application No. 2019-168683 filed on Sep. 17, 2019, the entire content of which is incorporated herein by reference.

TECHNOLOGICAL FIELD

The present disclosure relates to a medical instrument.

BACKGROUND DISCUSSION

Medical instruments such as catheters and guide wires which are to be inserted into a living body are required to exhibit an excellent lubricating property in order to reduce damage to tissues such as blood vessels and to improve operability by an operator. Therefore, a method of coating a surface of a base layer of a medical instrument with a hydrophilic polymer having a lubricating property has been developed and put into practical use. Meanwhile, in order to maintain the operability by an operator, it is also important that the hydrophilic polymer having a lubricating property can be maintained on the surface of the base layer when the operator uses the medical instrument. Therefore, not only an excellent lubricating property but also durability against loads such as abrasion and scratch is required in coating with the hydrophilic polymer.

From such viewpoints, Japanese Patent Application Publication 8-33704 A discloses a medical instrument in which a water-soluble or water-swellable polymer is dissolved in a solvent in which a base of the medical instrument swells to produce a polymer solution, the base of the medical instrument is immersed in the polymer solution to swell, the polymer is cross-linked or polymerized on a surface of a base layer, whereby a surface lubricating layer is formed on the surface of the base layer.

According to the technique disclosed in Japanese Patent Application Publication No. 8-33704 A, the surface lubricating layer exhibiting a favorable lubricating property can be fixed to the base.

Japanese Patent Application Publication No. 8-33704 A discloses that it is preferable to use, as the water-soluble or water-swellable polymer, a block copolymer having a hydrophilic site exhibiting a lubricating property and a site having an epoxy group. Further, in a case where such a block copolymer is used, the epoxy group of the block copolymer can be cross-linked by a heating operation, and the surface lubricating layer that is relatively difficult to peel off can be formed. However, a favorable lubricating property and excellent durability are in a trade-off relationship, and there is a need for a technique that enables compatibility of a favorable lubricating property and excellent durability.

In particular, in recent years, medical procedures allowing medical instruments with higher bendability to approach narrow lesion areas in a living body have been spreading. Operations with medical instruments continue for a relatively long time in some cases along with complication of the medical procedures. Therefore, in order to maintain favorable operability with devices even in a case of complicated lesion areas, there is a need for a technique that can further improve a lubrication retaining property (durability) of a device surface as compared with techniques in the related art. More specifically, there is a need for devices having excellent sliding durability that can maintain flexibility, and can maintain a relatively high lubricating property even in a case where sliding on a device surface is repeated.

Accordingly, there is a need for a technique that can improve durability (particularly, sliding durability) and can support medical procedures that are more complicated and sophisticated while maintaining flexibility of a medical instrument.

SUMMARY

The present disclosure provides means that can improve durability (particularly, sliding durability) of a surface lubricating layer while maintaining flexibility of a medical instrument.

In accordance with an exemplary embodiment, the present disclosure provides means that can improve durability (particularly, sliding durability) of a surface lubricating layer while maintaining flexibility of a medical instrument by providing, between a base whose surface is partially made of a polyester resin and a surface lubricating layer, an intermediate layer containing a (meth)acrylic-modified polyester resin and a polyurethane resin.

A medical instrument is disclosed, which includes: a base whose surface is partially made of a polyester resin; an intermediate layer formed on at least a part of the surface of the base and containing a (meth)acrylic-modified polyester resin and a polyurethane resin; and a surface lubricating layer formed on an upper part of the intermediate layer and containing a block copolymer having a structural unit (A) derived from a hydrophobic monomer and a structural unit (B) derived from a hydrophilic monomer, in which at least one of the hydrophobic monomer and the hydrophilic monomer has a (meth)acryloyl group.

A catheter is disclosed comprising: a surface that is partially made of a polyester resin; an intermediate layer formed on at least a part of the surface and containing a (meth)acrylic-modified polyester resin and a polyurethane resin; a surface lubricating layer formed on an upper part of the intermediate layer and containing a block copolymer having a structural unit derived from a hydrophobic monomer and a structural unit derived from a hydrophilic monomer; at least one of the hydrophobic monomer and hydrophilic monomer has a (meth)acryloyl group; and wherein the hydrophobic monomer contains at least one selected from the group consisting of glycidyl acrylate, glycidyl methacrylate, 3,4-epoxycyclohexylmethyl acrylate, 3,4-epoxycyclohexylmethyl methacrylate, and β-methylglycidyl methacrylate, and the hydrophilic monomer contains at least one selected from the group consisting of N,N-dimethylacrylamide, N,N-diethylacrylamide, acrylamide, 2-hydroxyethyl acrylate, and 2-hydroxyethyl methacrylate.

A method is disclosed of coating a medical instrument, the method comprising: applying an intermediate layer containing a (meth)acrylic-modified polyester resin and a polyurethane resin on at least a part of a surface of a base, the surface being partially made of a polyester resin; and applying a surface lubricating layer on an upper part of the intermediate layer, the surface lubricating layer containing a block copolymer having a structural unit derived from a hydrophobic monomer and a structural unit derived from a hydrophilic monomer, and wherein at least one of the hydrophobic monomer and the hydrophilic monomer has a (meth)acryloyl group.

BRIEF DESCRIPTION OF THE DRAWINGS

FIG. 3 is a table (Table 1) of (meth)acrylic-modified polyester resins 1 to 10 having (meth)acrylic modification ratios, contents of terephthalic acid, contents of isophthalic acid, and contents of polyhydric alcohol component and an unmodified polyester resin 11 not subjected to (meth)acrylic modification.

FIG. 4 is a table (Table 2) showing evaluation results of the coefficient of kinetic friction, the confirmation of the coating film on the intermediate layer, and the confirmation of the coating film on the surface lubricating layer, as well as the composition of the (meth)acrylic-modified polyester resin and the composition of the intermediate layer.

FIG. 5 is a table (Table 3) illustrating evaluation results of the elastic modulus and the sliding resistance increase rate.

DETAILED DESCRIPTION

Set forth below with reference to the accompanying drawings is a detailed description of embodiments of a medical instrument representing examples of the inventive medical instruments.

Figure 1:
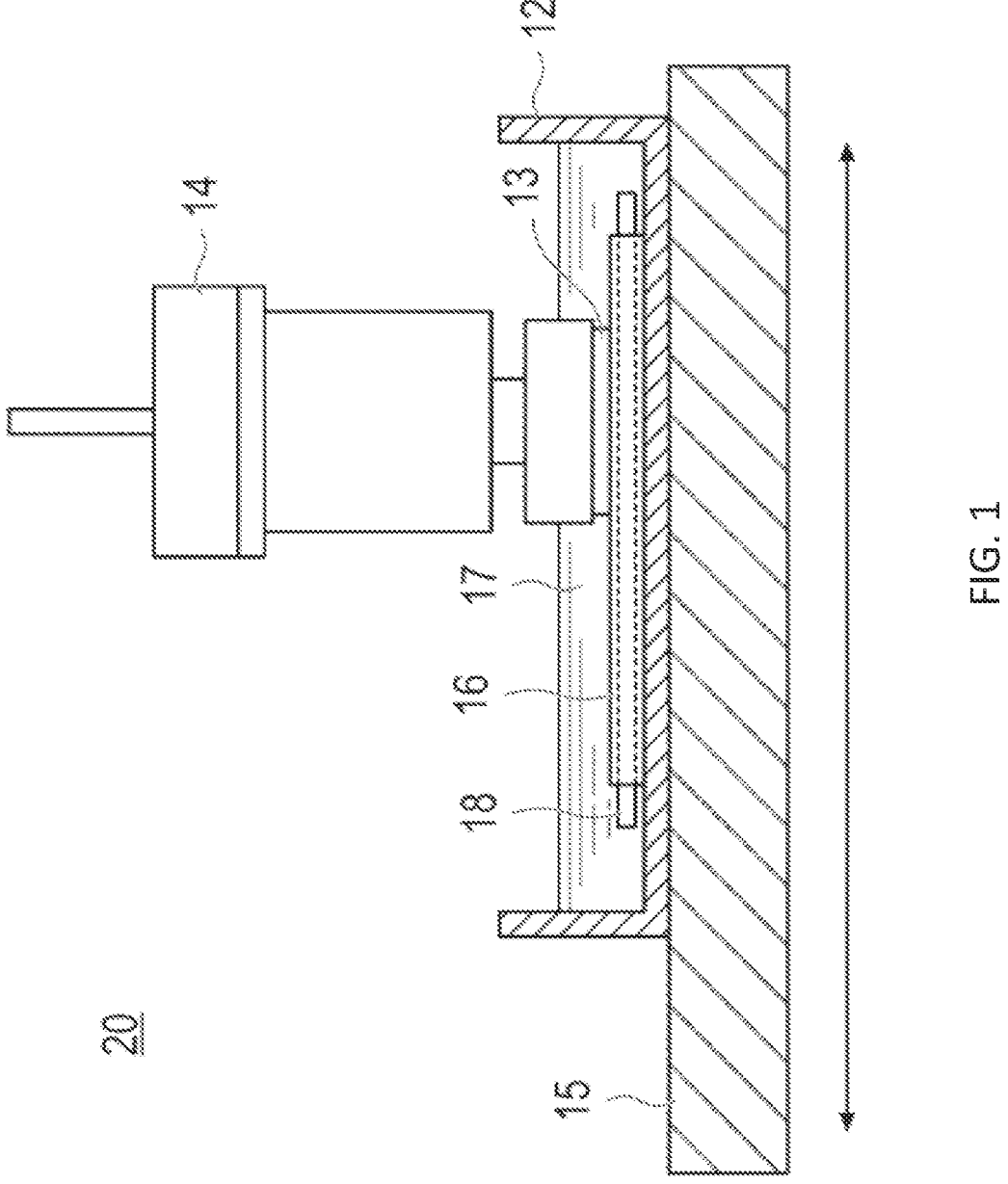
FIG. 1 is a schematic view of a friction measuring device used in examples.

In FIG. 1, reference numeral 12 denotes a petri dish, reference numeral 13 denotes an SEBS terminal, reference numeral 14 denotes a load, reference numeral 15 denotes a moving table, reference numeral 16 denotes a tube, reference numeral 17 denotes ion-exchanged water, reference numeral 18 denotes a core material, and reference numeral 20 denotes a friction measuring device.

That is, a medical instrument according to an embodiment of the present disclosure includes: a base whose surface is partially made of a polyester resin; an intermediate layer formed on at least a part of the surface of the base and containing a (meth)acrylic-modified polyester resin and a polyurethane resin; and a surface lubricating layer formed on an upper part of the intermediate layer and containing a block copolymer having a structural unit (A) derived from a hydrophobic monomer and a structural unit (B) derived from a hydrophilic monomer, in which at least one of the hydrophobic monomer and the hydrophilic monomer has a (meth) acryloyl group. The medical instrument according to the present disclosure having such a configuration is excellent in durability (particularly, sliding durability) of the surface lubricating layer while maintaining flexibility.

A mechanism by which the medical instrument according to the present disclosure can exhibit the excellent durability (sliding durability) of the surface lubricating layer while maintaining the flexibility is considered as follows. The present disclosure is not limited to the following estimation mechanism.

The block copolymer having a structural unit derived from a monomer having a (meth)acryloyl group and forming the surface lubricating layer exhibits a swelling property when in contact with a body fluid or an aqueous solvent, thus imparting a lubricating property (surface lubricating property) to the medical instrument and reducing friction with cavities such as blood vessel walls. Here, the (meth)acrylic-modified polyester resin contained in the intermediate layer according to the present disclosure has high affinity with the polyester resin contained in the surface of the base and also has high affinity with the block copolymer contained in the surface lubricating layer. In addition, since the polyurethane resin contained in the intermediate layer has high polarity, the polyurethane resin has affinity with both the polyester resin contained in the surface of the base and the block copolymer contained in the surface lubricating layer. Therefore, it is considered that, by providing the intermediate layer containing these two types of resins between the base and the surface lubricating layer, it is possible to strengthen adhesion between the base and the intermediate layer and adhesion between the intermediate layer and the surface lubricating layer, and improve durability (sliding durability) of the surface lubricating layer while maintaining flexibility of the base containing the polyester resin. Therefore, the medical instrument according to the present disclosure has excellent durability (sliding durability) of the surface lubricating layer while maintaining flexibility.

Hereinafter, embodiments of the present disclosure will be described. The present disclosure is not limited to the following embodiments. Dimensional ratios in the drawings are exaggerated for convenience of description and may differ from the actual ratios.

In the present description, "X to Y" indicating a range includes X and Y, and means "X or more and Y or less". Unless otherwise specified, operations, measurements of physical properties, and the like are performed under conditions of room temperature (20° C. to 25° C.) and relative humidity of 40% RH to 50% RH.

Further, in the present description, "(meth)acrylate" includes both methacrylate and acrylate, a "(meth)acryloyl group" includes both a methacryloyl group and an acryloyl group, and "(meta)acrylic" includes both methacrylic and acrylic.

Hereinafter, each component of the medical instrument will be described in detail.

Base

The surface of the base used in the present disclosure is partially made of a polyester resin. The base whose surface is partially made of a polyester resin has relatively good adhesion with the intermediate layer containing a (meth) acrylic-modified polyester resin and a polyurethane resin.

Examples of the polyester resin can include aliphatic polyester resins such as polylactic acid, polycaprolactone, and polybutylene succinate, and aromatic polyester resins such as polyethylene terephthalate, polytrimethylene terephthalate, and polybutylene terephthalate.

As the polyester resin according to the present disclosure, a polyester elastomer resin can also be used. The polyester elastomer resin is preferably a block copolymer containing a hard segment having crystallinity and a soft segment having noncrystallinity. Such a polyester elastomer resin can be softened by heat to exhibit fluidity, and exhibits rubber-like elasticity in a state where the heat is not applied.

A polyester elastomer may be a polyester-polyether type containing mainly an aromatic polyester resin as a hard segment and mainly containing an aliphatic polyether as a soft segment, or a polyester-polyester type containing mainly an aromatic polyester resin as a hard segment and mainly containing an aliphatic polyester as a soft segment.

The aromatic polyester resin contained in the hard segment, for example, is preferably polybutylene terephthalate, polyethylene terephthalate, or polytrimethylene terephthalate, and more preferably polybutylene terephthalate.

The soft segment of the polyester elastomer resin, for example, preferably contains an aliphatic polyether and/or an aliphatic polyester. Examples of the aliphatic polyether include polyethylene glycol, polypropylene glycol, poly (tetramethyleneoxy) glycol (polytetramethylene ether glycol), poly(hexamethyleneoxy) glycol, a copolymer of ethylene oxide and propylene oxide, an ethylene oxide addition polymer of polypropylene glycol, and a copolymer glycol of ethylene oxide and tetrahydrofuran. Examples of the aliphatic polyester include poly($\varepsilon$-caprolactone), polyenantholactone, polycaprylolactone, polybutylene adipate, and polyethylene adipate.

The polyester resins may be used alone or in combination of two or more of the polyester resins disclosed above.

Since the polyester resin has toughness, the polyester resin has followability that allows the medical instrument to smoothly proceed along a guide wire even in a complicated lesion site, and kink resistance that makes it difficult for the medical instrument to bend even in a curved part of a blood vessel even after the guide wire is pulled out. In particular, for example, in the case of the polyester elastomer resin, since the base of the medical instrument has toughness due to rigidity of a hard segment portion and flexibility of a soft segment portion, elongation of the base due to tension or twist can be further reduced.

As the polyester resin, a synthetic product or a commercially available product may be used. Examples of the commercially available product include: Pelprene® P type, S type, and EN type manufactured by Toyobo Co., Ltd.; Hytrel® SB654 and SB704 manufactured by Du Pont-Toray Co., Ltd.; and Tefabloc A series manufactured by Mitsubishi Chemical Corporation.

The base may contain other materials as long as the polyester resin is partially contained in the surface of the base. Examples of other materials can include a metal material, a polymer material (resin material or elastomer material) other than the polyester resin, and ceramics.

The metal material is not particularly limited, and a metal material generally used for a medical instrument such as a catheter, an introducer, a guide wire, and an indwelling needle can be used. Specific examples of the metal materials of the base can include various stainless steels such as SUS304, SUS314, SUS316, SUS316L, SUS420J2, and SUS630, gold, platinum, silver, copper, nickel, cobalt, titanium, iron, aluminum, tin, or various alloys such as nickel-titanium alloys, nickel-cobalt alloys, cobalt-chromium alloys, and zinc-tungsten alloys. These metal materials may be used alone or in combination of two or more of the metal materials. From the metal materials, the most suitable metal material may be appropriately selected as the base for the medical instrument such as a catheter, an introducer, a guide wire, and an indwelling needle, which are intended for use.

The polymer material (resin material or elastomer material) other than the polyester resin is not particularly limited, and a polymer material commonly used in the medical instrument such as a catheter, an introducer, a guide wire, and an indwelling needle is used. Specific examples of the polymer material can include polyamide resins, polyolefin resins such as a polyethylene resin and a polypropylene resin, modified polyolefin resins, cyclic polyolefin resins, epoxy resins, polyurethane resins, diallyl phthalate resins (allyl resins), polycarbonate resins, fluororesins, amino resins (a urea resin, a melamine resin, and a benzoguanamine resin), styrol resins, acrylic resins, polyacetal resins, vinyl acetate resins, phenol resins, vinyl chloride resins, silicone resins (silicon resins), polyether resins, and polyimide resins.

Thermoplastic elastomers such as a polyurethane elastomer and a polyamide elastomer can also be used as the material for the base.

These polymer materials may be used alone, or may be a mixture of two or more materials, or a copolymer of any two or more of the above resins or elastomers. From the polymer materials, the most suitable polymer material may be appropriately selected for the medical instrument such as a catheter, an introducer, a guide wire, and an indwelling needle, which are intended for use.

A shape of the base is not particularly limited, and is appropriately selected as a sheet shape, a linear shape (wire), and a tubular shape (tube), and the like depending on a form of the base to be used.

In accordance with an embodiment, the base may be entirely made of a polyester resin. If the polyester resin is contained on a part of the surface of the base, the base may be a multi-layer structure in which different materials are laminated in multiple layers, or may be a structure in which members made of different materials are joined to each part of the medical instrument. Further, the base may have a structure in which a surface of a core of the base made of any of the above materials is coated with a polyester resin and, if necessary, another material by an appropriate method, and a part of the surface contains a polyester resin.

Intermediate Layer

An intermediate layer is formed on at least a part of the base. In accordance with an embodiment, the intermediate layer may be formed on the whole or a part of the base, and it is preferable that the intermediate layer is formed on a region where the surface is made of a polyester resin. Another layer may be provided between the base and the intermediate layer as long as the another layer does not influence the action and effect of the present disclosure, and the intermediate layer is preferably located directly on the base.

(Meth)Acrylic-Modified Polyester Resin

The intermediate layer according to the present disclosure contains a (meth)acrylic-modified polyester resin. The (meth)acrylic-modified polyester resin is a resin formed by chemically bonding a (meth)acrylic resin segment to a polyester resin segment. In accordance with an embodiment, it may be preferable that the (meth)acrylic resin segment and the polyester resin segment are bonded to each other via a bireactive monomer.

(Meth)Acrylic Resin Segment

A (meth)acrylic polymerized segment constituting the (meth)acrylic-modified polyester resin is made of a resin obtained by polymerizing an addition-polymerizable monomer containing a (meth)acrylic monomer.

Examples of the (meth)acrylic monomer can include a (meth)acrylic acid ester monomer. Specific examples of (meth)acrylic monomer can include: acrylic acid esters such as methyl acrylate, ethyl acrylate, n-propyl acrylate, isopropyl acrylate, n-butyl acrylate, isobutyl acrylate, t-butyl acrylate, n-pentyl acrylate, n-hexyl acrylate, n-octyl acrylate, 2-ethylhexyl acrylate, stearyl acrylate, dodecyl acrylate, n-behenyl acrylate, n-tricosanyl acrylate, glycidyl acrylate, and phenyl acrylate; methacrylic acid esters such as methyl methacrylate, ethyl methacrylate, n-propyl methacrylate, isopropyl methacrylate, n-butyl methacrylate, isobutyl methacrylate, t-butyl methacrylate, n-pentyl methacrylate, n-hexyl methacrylate, n-octyl methacrylate, 2-ethylhexyl methacrylate, stearyl methacrylate, dodecyl methacrylate, n-behenyl methacrylate, n-tricosanyl methacrylate, glycidyl methacrylate, phenyl methacrylate, diethylaminoethyl methacrylate, dimethylaminoethyl methacrylate; acrylic acid; and methacrylic acid.

Among the (meth)acrylic monomers, n-butyl acrylate, methyl methacrylate, glycidyl methacrylate, and methacrylic acid are preferable.

These (meth)acrylic monomers may be used alone or in combination of two or more of the (meth)acrylic monomers.

The (meth)acrylic resin segment may have a structural unit derived from a general vinyl monomer in addition to a structural unit derived from the (meth)acrylic acid ester monomer described above. Examples of such a vinyl monomer can include: olefins such as ethylene, propylene, and isobutylene; vinyl esters such as vinyl propionate, vinyl acetate, and vinyl benzoate; vinyl ethers such as vinyl methyl ether, and vinyl ethyl ether; vinyl ketones such as vinyl methyl ketone, vinyl ethyl ketone, and vinyl hexyl ketone; N-vinyl compounds such as N-vinylcarbazole, N-vinylindole, and N-vinylpyrrolidone; vinyl compounds such as vinylnaphthalene and vinylpyridine; acrylonitrile; methacrylonitrile; and acrylamide.

In the present description, a content of the (meth)acrylic resin segment in the (meth)acrylic-modified polyester resin, that is, a ratio of the number of moles of monomers constituting the (meth)acrylic resin segment to a total number of moles of the monomers constituting the (meth)acrylic resin segment and monomers constituting the polyester resin segment is defined as a "(meth)acrylic modification ratio". The (meth)acrylic modification ratio can be, for example, preferably 5 mol % to 70 mol %, more preferably more than 10 mol % and 60 mol % or less, and still more preferably 30 mol % to 60 mol %. Within such a range, adhesion between the intermediate layer and the surface lubricating layer is further improved. The (meth)acrylic modification ratio can be calculated by analyzing the (meth)acrylic-modified polyester resin by a method such as pyrolysis gas chromatography mass spectrometry (Py-GC/MS) or ¹H-NMR.

Polyester Resin Segment

The polyester resin segment constituting the (meth)acrylic-modified polyester resin contains a polyester resin produced by subjecting a polycarboxylic acid component and a polyhydric alcohol component to a polycondensation reaction in the presence of an esterification catalyst.

Examples of the polycarboxylic acid component can include: dicarboxylic acids such as oxalic acid, succinic acid, maleic acid, adipic acid, β-methyladipic acid, azelaic acid, sebacic acid, nonanedicarboxylic acid, decandicarboxylic acid, undecanedicarboxylic acid, dodecanedicarboxylic acid, fumaric acid, citraconic acid, diglycolic acid, cyclohexane-3,5-diene-1,2-dicarboxylic acid, malic acid, citric acid, hexahydroterephthalic acid, malonic acid, pimelic acid, tartaric acid, mucic acid, phthalic acid, isophthalic acid, terephthalic acid, tetrahydrophthalic acid, p-carboxyphenylacetic acid, p-phenylenediacetic acid, m-phenylenediglycolic acid, p-phenylenediglycolic acid, o-phenylenediglycolic acid, diphenylacetic acid, diphenyl-p,p'-dicarboxylic acid, naphthalene-1,4-dicarboxylic acid, naphthalene-1,5-dicarboxylic acid, naphthalene-2,6-dicarboxylic acid, anthracenedicarboxylic acid, and dodecenylsuccinic acid; trimellitic acid; pyromellitic acid; naphthalenetricarboxylic acid; naphthalenetetracarboxylic acid; pyrenetricarboxylic acid; and pyrenetetracarboxylic acid. These polycarboxylic acid components can be used alone or in combination of two or more of the polycarboxylic acid components.

Among the polycarboxylic acid components, for example, it can be preferable to use terephthalic acid. That is, the (meth)acrylic-modified polyester resin according to the present disclosure preferably contains terephthalic acid as the polycarboxylic acid component. When terephthalic acid is contained, an elastic modulus of the (meth)acrylic-modified polyester resin is appropriately increased, and the adhesion between the base and the intermediate layer and the adhesion between the intermediate layer and the surface lubricating layer can be further improved.

A content of a structural unit derived from terephthalic acid in the (meth)acrylic-modified polyester resin can be, for example, preferably 5 mol % to 50 mol %, more preferably 10 mol % to 45 mol %, still more preferably 12.5 mol % to 40 mol %, even more preferably 12.5 mol % to 34 mol %, particularly preferably 13 mol % to 34 mol %, and more particularly preferably 13 mol % to 26 mol %, based on the total number of moles of the monomers constituting the (meth)acrylic resin segment and the monomers constituting the polyester resin segment. Within such a range, the adhesion of the intermediate layer to the base and the adhesion of the surface lubricating layer to the intermediate layer can be further improved.

The (meth)acrylic-modified polyester resin preferably further contains isophthalic acid as the polycarboxylic acid component. When isophthalic acid is contained, the elastic modulus of the intermediate layer is appropriate, and the adhesion between the base and the intermediate layer and the adhesion between the intermediate layer and the surface lubricating layer are further improved. The flexibility of the medical instrument is also easier to maintain. In a case where the (meth)acrylic-modified polyester resin contains isophthalic acid as the polycarboxylic acid component, the molar ratio of the structural unit derived from terephthalic acid to the structural unit derived from isophthalic acid in the (meth)acrylic-modified polyester resin can be, for example, preferably 1 or more and 5 or less, more preferably 1.5 or more and 4.5 or less, and still more preferably 1.8 or more and 4 or less. Within such a range, the adhesion between the base and the intermediate layer and the adhesion between the intermediate layer and the surface lubricating layer are further improved, and the durability (sliding durability) of the surface lubricating layer is excellent. Since the flexibility of the medical instrument can be rather easily maintained, the medical instrument has excellent followability to a bent portion.

The contents of terephthalic acid and isophthalic acid in the (meth)acrylic-modified polyester resin can be calculated by analyzing the (meth)acrylic-modified polyester resin by using the pyrolysis gas chromatography mass spectrometry (Py-GC/MS) or ¹H-NMR.

Specific examples of the polyhydric alcohol component include: dihydric alcohols such as ethylene glycol, propylene glycol, 1,3-propanediol, 1,4-butanediol, diethylene glycol, neopentyl glycol, hexanediol, cyclohexanediol, octanediol, decanediol, dodecanediol, polytetramethylene ether glycol, a bisphenol A-ethylene oxide adduct, and a bisphenol A-propylene oxide adduct; and trihydric or higher polyols such as glycerin, and pentaerythritol. These polyhydric alcohol components can be used alone or in combination of two or more of the polyhydric alcohol components.

Among the polyhydric alcohol components, ethylene glycol, 1,3-propanediol, 1,4-butanediol, diethylene glycol, neopentyl glycol, and polytetramethylene ether glycol are preferable, and ethylene glycol, diethylene glycol, and neopentyl glycol are more preferable.

When a dihydric alcohol is used as the polyhydric alcohol component, a content of a structural unit derived from the dihydric alcohol component in the (meth)acrylic-modified polyester resin can be, for example, preferably 5 mol % to 55 mol %, and preferably 10 mol % to 50 mol %, based on the total number of moles of the monomers constituting the (meth)acrylic resin segment and the monomers constituting the polyester resin segment.

The content of the polyester resin segment in the (meth)acrylic-modified polyester resin, that is, the ratio of the number of moles of the monomers constituting the polyester resin segment to the total number of moles of the monomers constituting the (meth)acrylic resin segment and the monomers constituting the polyester resin segment can be, for example, preferably 30 mol % to 95 mol %, more preferably 40 mol % or more and less than 90 mol %, and still more preferably 40 mol % to 70 mol %. The content of the polyester resin segment in the (meth)acrylic-modified polyester resin can also be calculated by analyzing the (meth)acrylic-modified polyester resin by using the pyrolysis gas chromatography mass spectrometry (Py-GC/MS) or $^1$H-NMR in the same manner as described above.

Bireactive Monomer

The bireactive monomer is a monomer that bonds the (meth)acrylic resin segment to the polyester resin segment, and is a monomer having both a functional group such as a hydroxy group, a carboxy group, an epoxy group, a primary amino group, and a secondary amino group that may form a polyester resin segment in a molecule, and an ethylenically unsaturated group that may form the (meth)acrylic resin segment in a molecule. The bireactive monomer is preferably a monomer having a hydroxy group or a carboxy group and an ethylenically unsaturated group.

Examples of the bireactive monomer can include a compound having a carboxy group and an ethylenically unsaturated group such as acrylic acid, methacrylic acid, maleic acid, itaconic acid, cinnamic acid, fumaric acid, maleic acid monoalkyl ester, and itaconic acid monoalkyl ester, and a compound having a hydroxy group and an ethylenically unsaturated group such as 2-hydroxyethyl (meth)acrylate, 2-hydroxypropyl (meth)acrylate, 3-hydroxypropyl (meth)acrylate, 2-hydroxybutyl (meth)acrylate, 3-hydroxybutyl (meth)acrylate, 4-hydroxybutyl (meth)acrylate, and polyethylene glycol mono(meth)acrylate. The polyester resin segment and the (meth)acrylic resin segment are bonded to each other via the bireactive monomer. These bireactive monomers can be used alone or in combination of two or more of the bireactive monomers.

Among the bireactive monomers, acrylic acid and methacrylic acid are preferable. In particular, methacrylic acid can be, for example, more preferable from the viewpoint of improving toughness of the (meth)acrylic-modified polyester resin. When methacrylic acid is used as the bireactive monomer, due to an effect of a steric hindrance of a methyl group of methacrylic acid, a polymerized chain of methacrylic acid is rather easily extended, and a bond distance between the (meth)acrylic resin segment and the polyester resin segment tends to be long. Therefore, it can be considered that a degree of freedom of the bonded portion between the (meth)acrylic resin segment and the polyester resin segment is further improved, and the toughness of the (meth)acrylic-modified polyester resin is further improved. Therefore, when methacrylic acid is used as the bireactive monomer, it is considered that the medical instrument has improved followability to the bent portion such as blood vessels.

A content of a structural unit derived from the bireactive monomer in the (meth)acrylic-modified polyester resin can be, for example, preferably 0.1 mol % to 20 mol %, and more preferably 1 mol % to 10 mol % based on a total number of moles of monomers constituting the (meth)acrylic-modified polyester resin. A content of the bireactive monomer can be calculated by analyzing the (meth)acrylic-modified polyester resin by a method such as pyrolysis gas chromatography mass spectrometry (Py-GC/MS) or $^1$H-NMR.

Method for Producing (Meth)Acrylic-Modified Polyester Resin

As a method for producing the (meth)acrylic-modified polyester resin using the bireactive monomer, the following three methods are preferable.

(1) A method in which the polyester resin segment is polymerized in advance, the polyester resin segment is reacted with the bireactive monomer, and monomers forming the (meth)acrylic resin segment are reacted so as to produce the (meth)acrylic-modified polyester resin.

(2) A method in which the (meth)acrylic resin segment is polymerized in advance, the (meth)acrylic resin segment is reacted with the bireactive monomer, and a polycarboxylic acid and a polyhydric alcohol forming the polyester resin segment are reacted so as to produce the (meth)acrylic-modified polyester resin.

(3) A method in which the polyester resin segment and the (meth)acrylic resin segment are separately polymerized in advance, and these segments are reacted with the bireactive monomer so as to bond both the segments to each other.

As a catalyst for synthesizing the polyester resin segment, various esterification catalysts can be used. Conditions in the esterification reaction are also not particularly limited.

The method for producing the (meth)acrylic resin segment is also not particularly limited, and examples of the method for producing the (meth)acrylic resin segment can include a method of performing, by using an oil-soluble or water-soluble polymerization initiator, polymerization by a polymerization method such as a bulk polymerization method, a solution polymerization method, an emulsion polymerization method, a miniemulsion method, and a dispersion polymerization method. If necessary, known chain transfer agents may be used. Conditions in the polymerization reaction are also not particularly limited.

Additionally, the following methods can be mentioned as the method for producing the (meth)acrylic-modified polyester resin. That is, a method of using a polycarboxylic acid having an ethylenically unsaturated group or a polyhydric alcohol having an ethylenically unsaturated group as a raw material monomer of the polyester resin segment, introducing the ethylenically unsaturated group into the polyester resin segment, and addition-polymerizing an addition-polymerizable monomer containing a (meth)acrylic monomer to a portion of the ethylenically unsaturated group. In addition, the (meth)acrylic-modified polyester resin may be produced by a method described in Japanese Patent Application Publication 2007-291546 A.

A weight average molecular weight (Mw) of the (meth)acrylic-modified polyester resin is preferably 10,000 or more from the viewpoint of increasing strength of the intermediate layer. The weight average molecular weight (Mw) of the (meth)acrylic-modified polyester resin can be measured by gel permeation chromatography (GPC) using polystyrene as a standard substance.

Polyurethane Resin

The polyurethane resin can impart elasticity to the medical instrument. Therefore, the medical instrument provided with the intermediate layer containing the polyurethane resin has good followability even in a highly bendable portion.

The polyurethane resin used in the present disclosure is not particularly limited, and for example, a polyurethane resin obtained by reacting (i) a component containing an average of two or more active hydrogens in one molecule and (ii) a polyisocyanate component can be used.

As the polyurethane resin, for example, a polyurethane resin produced by chain-extending, with a chain extender, an isocyanate group-containing prepolymer, which is obtained by subjecting the above components (i) and (ii) to an urethanization reaction, and adding water to form a dispersion can be used. The prepolymer may be obtained by subjecting the above components (i) and (ii) to an urethanization reaction under a condition where an isocyanate group is excessive. The urethanization reaction may be carried out in an organic solvent that is inert to the reaction and has high affinity with water. Further, the prepolymer may be neutralized prior to chain extension of the prepolymer. Examples of a method for chain-extending the isocyanate group-containing prepolymer include a method in which the isocyanate group-containing prepolymer and the chain extender are reacted in the presence of a catalyst, if necessary. At the time, as the chain extender, water, water-soluble polyamines, glycols, and the like are used.

As the component (i), those having hydroxy-based active hydrogen are preferable, and for example, a compound having an average of two or more hydroxy groups in one molecule is preferable. Specific examples of the component (i) include (1) a polyol compound, (2) a polyether polyol compound, (3) a polyester polyol compound, (4) a polyether ester polyol compound, and (5) a polycarbonate polyol compound. Hereinafter, the compounds (1) to (5) will be described.

(1) Polyol Compound

Examples of the polyol compound include ethylene glycol, propylene glycol, diethylene glycol, triethylene glycol, 1,2-butylene glycol, 1,3-butylene glycol, 2,3-butylene glycol, 1,4-butylene glycol, 1,5-pentanediol, neopentyl glycol, 1,6-hexane glycol, 2,5-hexanediol, dipropylene glycol, 2,2,4-trimethyl-1,3-pentanediol, tricylcodecanedimethanol, 1,4-cyclohexanedimethanol, 2,2-dimethylpropane diol, 1,4-butanediol, 1,6-hexanediol, 1,8-octamethylenediol, glycerin, trimethylolpropane, bisphenol A, bisphenol E, bisphenol F, phenol novolac, and cresol novolac.

(2) Polyether Polyol Compound

Examples of the polyether polyol compound include: an alkylene oxide adduct of the polyol compound in the above (1); a ring-opening (co)polymer of an alkylene oxide and a cyclic ether (for example, tetrahydrofuran); polyethylene glycol; polypropylene glycol; a copolymer of ethylene glycol and propylene glycol; a copolymer of ethylene glycol and 1,4-butanediol; polytetramethylene glycol; polyhexamethylene glycohol; and polyoctamethylene glycol.

(3) Polyester Polyol Compound

Examples of the polyester polyol compound include those obtained by polycondensing a polycarboxylic acid or an anhydrate of a polycarboxylic acid and the polyol compound in the above (1) under a condition where the hydroxy group is excessive. Here, examples of the polycarboxylic acid can include: dicarboxylic acids such as adipic acid, succinic acid, sebacic acid, glutaric acid, maleic acid, fumaric acid, phthalic acid, isophthalic acid, and terephthalic acid; and tricarboxylic acids such as trimellitic acid. More specific examples of the polyester polyol compound include an ethylene glycol-adipic acid condensate, a butanediol-adipic acid condensate, a hexamethylene glycol-adipic acid condensate, an ethylene glycol-propylene glycol-adipic acid condensate, or a polylactone diol obtained by ring-opening polymerization of lactone using glycol as an initiator.

(4) Polyether Ester Polyol Compound

Examples of the polyether ester polyol compound include those obtained by mixing an ether group-containing polyol or a mixture of the ether group-containing polyol and other glycols with the polycarboxylic acid or an anhydrate of the polycarboxylic acid as shown in the above (3), and reacting the obtained mixture with an alkylene oxide. Examples of the ether group-containing polyol include the polyether polyol in the above (2), and diethylene glycol. Examples of the polyether ester polyol can include a polytetramethylene glycol-adipic acid condensate.

(5) Polycarbonate Polyol Compound

Examples of the polycarbonate polyol compound include compounds represented by a general formula HO—R—(O—C(O)—O—R)X—OH (in the formula, R represents a saturated fatty acid polyol residue having 1 to 12 carbon atoms, and x indicates the number of repeating units, which is usually an integer of 5 to 50). The polycarbonate polyol compound can be obtained by a transesterification method in which a saturated aliphatic polyol and a substituted carbonate (for example, diethyl carbonate or diphenyl carbonate) are reacted under the condition where the hydroxy group is excessive, and a method in which a saturated aliphatic polyol is reacted with phosgene, and if necessary, the saturated aliphatic polyol is further reacted.

The above components (i) can be used alone or in combination of two or more the above components (i).

From the viewpoint of increasing durability (toughness) of the intermediate layer, it is preferable that the polyurethane resin according to the present disclosure has a high elastic modulus. Therefore, the component (i) preferably contains bisphenols such as bisphenol A, bisphenol E, and bisphenol F, and more preferably contains bisphenol A.

In accordance with an embodiment, when the elastic modulus of the polyurethane resin according to the present disclosure is too high, the intermediate layer is brittle, and the adhesion between the base and the intermediate layer and the adhesion between the intermediate layer and the surface lubricating layer may decrease. From such a viewpoint, the elastic modulus of the polyurethane resin according to the present disclosure can be, for example, preferably 250 MPa to 800 MPa, and more preferably 300 MPa to 500 MPa.

Examples of the component (ii) (that is, the polyisocyanate component) that reacts with the component (i) include a compound (polyisocyanate compound) containing an average of two or more isocyanate groups in one molecule. The compound may be an aliphatic compound, an alicyclic compound, an aromatic compound, or an aromatic aliphatic compound.

Examples of the aliphatic polyisocyanate compound include trimethylene diisocyanate, tetramethylene diisocyanate, pentamethylene diisocyanate, hexamethylene diisocyanate, 1,2-propylene diisocyanate, 2,3-butylene diisocyanate, 1,3-butylene diisocyanate, dodecamethylene diisocyanate, and 2,4,4-trimethylhexamethylene diisocyanate.

Examples of the alicyclic polyisocyanate compound include 3-isocyanatomethyl-3,5,5-trimethylcyclohexyl isocyanate, 1,3-cyclopentane diisocyanate, 1,3-cyclohexane diisocyanate, 1,4-cyclohexane diisocyanate, methyl-2,4-cyclohexane diisocyanate, methyl-2,6-cyclohexane diisocyanate, 4,4'-methylene bis(cyclohexyl isocyanate), 1,4-bis(isocyanatemethyl) cyclohexane, and 1,4-bis(isocyanatemethyl) cyclohexane.

Examples of the aromatic polyisocyanate compound include 1,3-phenylene diisocyanate, 4,4'-diphenyl diisocyanate, 1,4-phenylene diisocyanate, 4,4'-diphenylmethane diisocyanate, 2,4-tolylene diisocyanate, 2,6-tolylene diisocyanate, 4,4'-toluidine diisocyanate, 2,4,6-triisocyanatotoluene, 1,3,5-triisocyanatobenzene, dianisidine diisocyanate, 4,4'-diphenyl ether diisocyanate, and 4,4',4"-triphenylmethane triisocyanate.

Examples of the aromatic aliphatic polyisocyanate compound include m-xylylene diisocyanate, $\omega,\omega'$-diisocyanate-1,3-dimethylbenzene, $\omega,\omega'$-diisocyanate-1,4-dimethylbenzene, $\omega,\omega'$-diisocyanate-1,4-diethylbenzene, 1,4-tetramethylxylylene diisocyanate, and 1,3-tetramethylxylylene diisocyanate.

The polyisocyanate compound is a diisocyanate compound, and a triisocyanate compound obtained by modifying the diisocyanate compound can also be used as the component (ii). Examples of the triisocyanate compound include a trimethylolpropane adduct, a biuret, and a trimer (the trimer contains an isocyanurate ring) of the diisocyanate compound.

These components (ii) can be used alone or in combination of two or more of the components (ii).

As the polyurethane resin, a commercially available water-based urethane resin may be used. The water-based urethane resin is a composition containing the polyurethane resin and water, and is usually a composition in which the polyurethane resin and any components contained as necessary are dispersed in water. Examples of the commercially available water-based urethane resin include "Adekabontiter®" series manufactured by ADEKA Corporation, "Olester®" series manufactured by Mitsui Chemicals Corporation, "Vondic®" series manufactured by DIC Corporation, "Hydran®" series, "Impranil®" series manufactured by Bayer Corporation, "Sanprene®" series manufactured by Sanyo Chemical Industries, Ltd., "Super Flex" series and F-2170D manufactured by DKS Co., Ltd., "NEOREZ®" series manufactured by Kusumoto Chemicals, Ltd., and "Sancure®" series manufactured by Lubrizol Japan Ltd.

These polyurethane resins may be used alone or in combination of two or more of the polyurethane resins.

A weight average molecular weight (Mw) of the polyurethane resin is preferably 10,000 or more from the viewpoint of increasing the strength of the intermediate layer. The weight average molecular weight (Mw) of the polyurethane resin can be measured by gel permeation chromatography (GPC) using polystyrene as a standard substance.

A mass ratio of the (meth)acrylic-modified polyester resin to the polyurethane resin in the intermediate layer can be, for example, preferably (meth)acrylic-modified polyester resin/polyurethane resin=10/90 to 90/10, and more preferably 70/30 to 30/70. Within such a range, it is possible to obtain a medical instrument having further improved durability (sliding durability) of the surface lubricating layer while maintaining flexibility.

Other Components

The intermediate layer may contain other components in addition to the (meth)acrylic-modified polyester resin and the polyurethane resin. The other components are not particularly limited, and examples of the other components can include: silane coupling agents such as acrylic-modified silane coupling agents; inorganic fillers such as silica; reactive colloidal silica; polyvinyl compounds such as polyvinyl ether and polyvinyl alcohol; polyamide resins; and acrylic polyols.

Method for Forming Intermediate Layer

A method for forming the intermediate layer according to the present disclosure is not particularly limited, and preferably includes coating the base with a solution (also simply referred to herein as a "coating solution for the intermediate layer") containing the (meth)acrylic-modified polyester resin, the polyurethane resin, a solvent, and if necessary, other components ((I-a) solution coating step, coating layer forming step), and drying the coating layer ((I-b) drying step).

(I-a) Solution Coating Step (Coating Layer Forming Step)

In the method for forming the intermediate layer according to the present disclosure, first, the base is coated with the solution containing the (meth)acrylic-modified polyester resin, the polyurethane resin, the solvent, and if necessary, other components ((I-a) solution coating step, coating layer forming step). The solution coating step is performed for the purpose of supporting (or covering) the intermediate layer containing the (meth)acrylic-modified polyester resin and the polyurethane resin on an upper part of the base. The expression "supporting" means a state where the intermediate layer is immobilized so as not to be relatively easily released from the surface of the base, and can include not only a form in which the entire surface of the base is completely covered by the intermediate layer, but also a form in which only a part of the surface of the base is covered by the intermediate layer, that is, a form in which the intermediate layer is attached only to a part of the surface of the base. Therefore, the method coating with the coating solution for the intermediate layer is not particularly limited as long as the solution containing the (meth)acrylic-modified polyester resin, the polyurethane resin, and the solvent is used, and a method same as a known method or an appropriate modification of a known method can be applied.

In the solution coating step, specifically, the (meth)acrylic-modified polyester resin, the polyurethane resin, and if necessary, other components are dissolved in the solvent to prepare the solution (coating solution for the intermediate layer), and the base is coated with the solution (coating solution) to form a coating layer.

The solvent used in the step is not particularly limited as long as the solvent can dissolve the (meth)acrylic-modified polyester resin and the polyurethane resin according to the present disclosure. Examples of the solvent can include water, alcohols such as methanol, ethanol, 1-propanol, isopropanol, and ethylene glycol, ketones such as acetone, methyl ethyl ketone, and cyclohexanone, esters such as ethyl acetate, halides such as chloroform, olefins such as hexane, ethers such as tetrahydrofuran (THF) and butyl ether, aromatics such as benzene and toluene, amides such as N,N-dimethylformamide (DMF), and sulfoxides such as dimethyl sulfoxide, but the solvent is not limited thereto. The solvents may be used alone or in combination of two or more of the solvents. Among the solvents, from the viewpoint that the (meth)acrylic-modified polyester resin and the polyurethane resin can be uniformly dissolved, and the solution can be applied uniformly, the solvent is preferably water and alcohols in combination, and a mixed solvent of water and 1-propanol is particularly preferable.

Preparation of Coating Solution for Intermediate Layer

The coating solution for the intermediate layer is prepared using the (meth)acrylic-modified polyester resin, the polyurethane resin, the solvent, and if necessary, other components. An order and a method of adding the above components are not particularly limited. The above components may be added collectively or separately, stepwise or continuously. In addition, a mixing method is not particularly limited, and a known method can be used. A preferred method for preparing the coating solution for the intermediate layer includes sequentially adding the (meth)acrylic-modified polyester resin and the polyurethane resin to the solvent and stirring the resins in the solvent.

A concentration of the (meth)acrylic-modified polyester resin and the polyurethane resin in the solution (coating solution for the intermediate layer) is not particularly limited. From the viewpoint of further improving a coating property, the concentration (solid concentration) of the (meth)acrylic-modified polyester resin and the polyurethane resin in the coating solution can be, for example, preferably 0.01% by mass to 20% by mass, more preferably 0.05% by mass to 15% by mass, and still more preferably 1% by mass or more and less than 15% by mass. When a concentration of the block copolymer is in the above range, the adhesion and the like of the obtained intermediate layer may be sufficiently exhibited. In addition, a uniform intermediate layer with a desired thickness can be easily obtained with a single coating, and the viscosity of the solution is within an appropriate range, which is preferable in terms of operability (for example, ease of coating) and production efficiency. However, even when the concentration deviates from the above range, the intermediate layer can be sufficiently used as long as functions and effects of the present disclosure are not influenced.

Coating with Coating Solution for Intermediate Layer

Next, after preparing the coating solution for the intermediate layer as described above, the base is coated with the coating solution.

A method of coating the surface of the base with the coating solution for the intermediate layer is not particularly limited, and methods such as a coating and printing method, an immersion method (dipping method, dip coating method), a spraying method (spray method), a spin coating method, a mixed solution impregnated sponge coating method, a bar coating method, a die coating method, a reverse coating method, a comma coating method, a gravure coating method, and a doctor knife method can be applied.

When the intermediate layer is to be formed on a thin and narrow inner surface of a catheter, an injection needle, or the like, the base may be immersed in the coating solution and defoaming is performed while reducing a pressure in the system. By performing defoaming while reducing the pressure, the solution can be quickly permeated into the thin and narrow inner surface and formation of the intermediate layer can be promoted.

When the intermediate layer is to be formed only on a part of the base, by immersing only the part of the base in the coating solution to coat the part of the base with the coating solution, the intermediate layer can be formed on a desired surface portion of the base.

When it is difficult to immerse only the part of the base in the coating solution, upon protecting (covering, and the like) in advance, with an appropriate member or material that can be attached and detached (mounted and dismounted), a surface portion of the base where the intermediate layer is not required to be formed, the base is immersed in the coating solution to coat the base with the coating solution, then the protective member (material) on the surface portion of the base where the intermediate layer is not required to be formed is removed, and then a drying treatment or the like is performed, thereby forming the intermediate layer on the desired surface portion of the base. However, the present disclosure is not limited to these forming methods, and the intermediate layer can be formed by appropriately using known methods. For example, when it is difficult to immerse only the part of the base in the coating solution, another coating method (for example, a method of coating a predetermined surface portion of a medical instrument with a coating solution by using a coating device such as a spray device, a bar coater, a die coater, a reverse coater, a comma coater, a gravure coater, a spray coater, and a doctor knife) may be applied instead of the immersion method. When a structure of the medical instrument is required to include an intermediate layer in both an outer surface and an inner surface of a cylindrical tool of the medical instrument, the immersion method (dipping method) is preferably used because both the outer surface and the inner surface can be coated at one time.

A coating amount of the coating solution for the intermediate layer can be, for example, preferably such that a thickness of the obtained coating film (intermediate layer) is 1 nm to 1000 nm, and more preferably 100 nm to 500 nm. With a coating amount having a thickness of 1 nm to 1000 nm, adhesion of the obtained coating film (intermediate layer) to the base can be sufficiently achieved (I-b) Drying Step In the method for forming the intermediate layer according to the present disclosure, it is preferable to perform a drying step after coating the base with the coating solution for the intermediate layer to form the coating layer.

A drying temperature is not particularly limited, and the drying temperature can be, for example, preferably 10° C. to 200° C., and more preferably 25° C. to 150° C. A drying time is not particularly limited, and can be, for example, preferably 5 minutes to 5 hours, and more preferably 10 minutes to 3 hours.

A pressure condition during drying is not limited, and the drying step may be performed under a normal pressure (atmospheric pressure), or under a pressure or a reduced pressure. As a drying means (device), for example, a drying oven, an oven, a vacuum dryer, or the like can be used.

Surface Lubricating Layer

The surface lubricating layer is formed on an upper part of the intermediate layer. Here, the surface lubricating layer is preferably formed on only the upper part of the intermediate layer provided on a portion whose surface is required to have a lubricating property when wet. It is needless to say that the surface lubricating layer may be provided so as to cover the entire intermediate layer.

The surface lubricating layer according to the present disclosure contains a block copolymer having a structural unit (A) derived from a hydrophobic monomer and a structural unit (B) derived from a hydrophilic monomer. In the present description, the structural unit (A) derived from the hydrophobic monomer is also simply referred to as "structural unit derived from the hydrophobic monomer" or "structural unit (A)". Similarly, the structural unit (B) derived from the hydrophilic monomer is also simply referred to as "structural unit derived from the hydrophilic monomer" or "structural unit (B)". The block copolymer having the structural unit (A) derived from the hydrophobic monomer or the structural unit (B) derived from the hydrophilic monomer is also simply referred to as "block copolymer".

Block Copolymer

The surface lubricating layer according to the present disclosure contains the block copolymer having the structural unit (A) derived from the hydrophobic monomer and the structural unit (B) derived from the hydrophilic monomer. At least one of the hydrophobic monomer and the hydrophilic monomer has a (meth)acryloyl group. Such a block copolymer has excellent affinity with the (meth)acrylic-modified polyester resin and the polyurethane resin contained in the intermediate layer, and the surface lubricating layer containing the block copolymer has higher adhesion with the intermediate layer. Therefore, the surface lubricating layer according to the present disclosure is excellent in durability (sliding durability).

As mentioned above, at least one of the hydrophobic monomer and the hydrophilic monomer has a (meth)acryloyl group. That is, examples of the block copolymer can include, for example, three forms, that is, (a) a form in which the hydrophobic monomer has a (meth)acryloyl group and the hydrophilic monomer does not have a (meth)acryloyl group ("form (a)"), (b) a form in which the hydrophilic monomer has a (meth)acryloyl group and the hydrophobic monomer does not have a (meth)acryloyl group ("form (b)"), and (c) a form in which both the hydrophobic monomer and the hydrophilic monomer have a (meth)acryloyl group ("form (c)"). The forms can be used without limitation. However, from the viewpoint of further improving the effect of the present disclosure, the above form (c) can be, for example, preferable.

Hydrophobic Monomer

The hydrophobic monomer constituting the block copolymer will be described. In the present description, the "hydrophobic monomer" is referred to as a compound having a dissolution amount of 0.1 g or less in 100 g of water at 20° C.

The hydrophobic monomers may be used alone or in combination of two or more of the hydrophobic monomers. That is, a hydrophobic unit (hydrophobic site) derived from the hydrophobic monomer may be a homopolymer type including only one kind of hydrophobic monomer, or a copolymer type including two or more kinds of hydrophobic monomers. When two or more kinds of hydrophobic monomers are used, a form of the hydrophobic site may be a block copolymer, a random copolymer, or an alternating copolymer.

The hydrophobic monomer constituting the block copolymer is not particularly limited as long as the hydrophobic monomer satisfies the above definition, and a known compound can be used. Examples of such a hydrophobic monomer can include a monomer having a (meth)acryloyl group such as: (meth)acrylic acid esters having a glycidyl group (epoxy group) such as glycidyl acrylate, glycidyl methacrylate (GMA), 3,4-epoxycyclohexylmethyl acrylate, 3,4-epoxycyclohexylmethyl methacrylate, β-methylglycidyl acrylate, and 3-methylglycidyl methacrylate; (meth)acrylic acid esters having an alkyl group having 1 carbon atoms to 24 carbon atoms such as methyl acrylate, methyl methacrylate, ethyl acrylate, ethyl methacrylate, isopropyl acrylate, isopropyl methacrylate, n-propyl acrylate, n-propyl methacrylate, n-butyl acrylate, n-butyl methacrylate (BuMA), 2-ethylhexyl acrylate, and 2-ethylhexyl methacrylate; (meth) acrylic acid esters having an aryl group having 6 carbon atoms to 20 carbon atoms such as phenyl acrylate and phenyl methacrylate; (meth)acrylic acid esters having an aralkyl group having 7 carbon atoms to 30 carbon atoms such as benzyl acrylate and benzyl methacrylate; and N-alkylacrylamides such as N-tert-butylacrylamide and N-tert-butyl methacrylamide.

A hydrophobic monomer having no (meth)acryloyl group such as: vinyl ethers having a glycidyl group (epoxy group) such as allyl glycidyl ether; olefins such as ethylene, propylene, isobutylene, vinyl chloride, and vinylidene chloride; aromatic vinyls such as styrene and α-methylstyrene; and vinyl esters such as vinyl propionate can also be used in the form (b). Further, if the hydrophobic unit (hydrophobic site) derived from the hydrophobic monomer is a copolymer type including a hydrophobic monomer having a (meth)acryloyl group and a hydrophobic monomer having no (meth)acryloyl group, the hydrophobic monomer having no (meth) acryloyl group can be used also in the form (a) and the form (c).

Among the above, the hydrophobic monomer preferably contains at least one selected from the group consisting of glycidyl acrylate, glycidyl methacrylate, 3,4-epoxycyclohexylmethyl acrylate, 3,4-epoxycyclohexylmethyl methacrylate, β-methylglycidyl acrylate, β-methylglycidyl methacrylate, methyl acrylate, methyl methacrylate, n-butyl acrylate, n-butyl methacrylate, 2-ethylhexyl acrylate, 2-ethylhexyl methacrylate, benzyl acrylate, and benzyl methacrylate.

Further, from the viewpoints of further improving the adhesion with the intermediate layer and further enhancing the durability (sliding durability) of the surface lubricating layer, the hydrophobic monomer more preferably contains at least one selected from the group consisting of glycidyl acrylate, glycidyl methacrylate, 3,4-epoxycyclohexylmethyl acrylate, 3,4-epoxycyclohexylmethyl methacrylate, and β-methylglycidyl methacrylate. Particularly preferably, the hydrophobic monomer is glycidyl acrylate or glycidyl methacrylate. These hydrophobic monomers have an epoxy group (glycidyl group), and due to bias of a charge distribution of the epoxy group (glycidyl group), a cohesive force between the hydrophobic sites can be generated, and a polymer chain can be easily entangled. Therefore, it is considered that the durability (sliding durability) of the surface lubricating layer is further improved.

Hydrophilic Monomer

The hydrophilic monomer will be described. In the present description, the "hydrophilic monomer" is referred to as a compound in which, when a block copolymer having the hydrophilic monomer and the structural unit derived from the hydrophobic monomer is prepared, the block copolymer has a swelling property when in contact with a body fluid or an aqueous solvent, and can impart a lubricating property (surface lubricating property) to the medical instrument. By introducing the structural unit (B) derived from such a hydrophilic monomer into the block copolymer, the medical instrument exhibits a lubricating property (surface lubricating property), and friction when the medical instrument is in contact with cavities such as blood vessel walls can be reduced.

The hydrophilic monomers may be used alone or in combination of two or more of the hydrophilic monomers. That is, a hydrophilic unit (hydrophilic site) derived from the hydrophilic monomer may be a homopolymer type including only one kind of hydrophilic monomer, or a copolymer type including two or more kinds of hydrophilic monomers. When two or more kinds of hydrophilic monomers are used, a form of the hydrophilic site may be a block copolymer, a random copolymer, or an alternating copolymer.

The hydrophilic monomer constituting the block copolymer is not particularly limited as long as the hydrophobic monomer satisfies the above definition, and a known compound can be used. Examples of such a hydrophilic monomer can include a monomer having a (meth)acryloyl group such as acrylic acid, methacrylic acid, maleic acid, 2-acrylamide-2-methylpropanesulfonic acid, (meth)acryloyloxy-ethyltrimethyl ammonium salts, (3-acryloylaminopropyl) trimethylammonium salts, (3-methacryloylaminopropyl) trimethylammonium salts, N-methylacrylamide, N,N-dimethylacrylamide (DMAA), N-ethylacrylamide, acrylamide, N,N-diethylacrylamide (DEAA), N,N-dimethylaminopropyl acrylamide, N,N-dimethylaminopropyl methacrylamide, N,N-dimethylaminoethyl acrylate, N,N-dimethylaminoethyl methacrylate, 2-hydroxyethyl acrylate, 2-hydroxyethyl methacrylate, 3-hydroxypropyl acrylate, 3-hydroxypropyl methacrylate, polyethylene glycol monoacrylate, polyethyleneglycol monomethacrylate, alkoxy polyethylene glycol monoacrylate, and alkoxy polyethylene glycol monomethacrylate.

A hydrophilic monomer having no (meth)acryloyl group, such as N-vinyl-2-pyrrolidone, can also be used in the form (a). Further, if the hydrophilic unit (hydrophilic site) derived from the hydrophilic monomer is a copolymer type including a hydrophilic monomer having a (meth)acryloyl group and a hydrophilic monomer having no (meth)acryloyl group, the hydrophobic monomer having no (meth)acryloyl group can be used also in the form (b) and the form (c).

Among the above, from the viewpoints of exhibiting an excellent surface lubricating property, further improving the adhesion with the intermediate layer, and further enhancing the durability (sliding durability) of the surface lubricating layer, the hydrophilic monomer preferably contains at least one selected from the group consisting of N,N-dimethylacrylamide, N,N-diethylacrylamide, acrylamide, 2-hydroxyethyl acrylate, and 2-hydroxyethyl methacrylate. The hydrophilic monomer is more preferably N,N-dimethylacrylamide or N,N-diethylacrylamide, and particularly preferably N,N-dimethylacrylamide.

Ratio (Composition Ratio) of Structural Units

A ratio (composition ratio) of the structural unit (A) to the structural unit (B) in the block copolymer is not particularly limited as long as the above effects are achieved. Considering a good lubricating property, lubrication retaining property, slidability, sliding durability, strength of a coating layer, adhesion with the base layer, and the like, the ratio of the structural unit (A) to the structural unit (B) (molar ratio of the structural unit (A) to the structural unit (B)) can be, for example, preferably 1:2 to 1:100, more preferably 1:5 to 1:50, and still more preferably 1:10 to 1:20. Within such a range, the surface lubricating layer can sufficiently exhibit a lubricating property, and the adhesion to the intermediate layer and the sliding durability can be further improved. The molar ratio of the structural unit (A) to the structural unit (B) can be controlled by adjusting a charging ratio (molar ratio) of monomers at a stage of producing the block copolymer. At this time, the charging ratio (molar ratio) of the hydrophobic monomer to the hydrophilic monomer in the stage of producing the block copolymer can be, for example, preferably 1:2 to 1:100, more preferably 1:5 to 1:50, and still more preferably 1:10 to 1:20. The molar ratio of the structural unit (A) to the structural unit (B) can be confirmed, for example, by performing NMR measurement ($^1$H-NMR measurement, $^{13}$C-NMR measurement, and the like) on the copolymer.

Weight Average Molecular Weight (Mw) of Block Copolymer

A weight average molecular weight of the block copolymer is not particularly limited, and can be, for example, preferably 10,000 to 10,000,000 from the viewpoint of solubility. Further, the weight average molecular weight of the block copolymer is more preferably 100,000 to 5,000,000 from the viewpoint of ease of preparation of a block copolymer solution (coating solution for the surface lubricating layer). As the weight average molecular weight of the block copolymer, a value measured by gel permeation chromatography (GPC) using polystyrene as a standard substance is adopted.

Method for Producing Block Copolymer

A method for producing the block copolymer is not particularly limited, and the block copolymer can be produced by applying a polymerization method known in the related art such as a living radical polymerization method, a polymerization method using a macroinitiator, and a polycondensation method. Among polymerization methods, the living radical polymerization method or the polymerization method using the macroinitiator is preferably used since it is easy to control molecular weights and molecular weight distributions of the structural unit (site) derived from the hydrophobic monomer and the structural unit (site) derived from the hydrophilic monomer. The living radical polymerization method is not particularly limited, and for example, methods described in Japanese Patent Application Publication No. 11-263819 A, Japanese Patent Application Publication No. 2002-145971 A, and Japanese Patent Application Publication No. 2006-316169 A, and an atom transfer radical polymerization (ATRP) method can be applied in the same manner or appropriately modified. In the polymerization method using the macroinitiator, for example, the macroinitiator having a hydrophobic site having a hydrophobic functional group and a radically polymerizable group such as a peroxide group is produced, and then the macroinitiator and the monomer for forming the hydrophilic site (hydrophilic unit) are polymerized, whereby the block copolymer having a hydrophilic site (hydrophilic unit) and a hydrophobic site (hydrophobic unit) can be produced.

In the polymerization of the block copolymer, known methods such as bulk polymerization, suspension polymerization, emulsion polymerization, and solution polymerization can be used. Specifically, in the production of the block copolymer, solution polymerization in which a hydrophobic monomer and a hydrophilic monomer are copolymerized by stirring and heating together with a polymerization initiator in a polymerization solvent can be applied. Here, the polymerization initiator is not particularly limited, and known initiators may be used. The polymerization solvent is not particularly limited, and for example, aliphatic organic solvents such as n-hexane, n-heptane, n-octane, n-decane, cyclohexane, methylcyclohexane, and liquid paraffin, ether-based solvents such as tetrahydrofuran and dioxane, aromatic organic solvents such as benzene, toluene, and xylene, halogen-based organic solvents such as 1,2-dichloroethane and chlorobenzene, and polar aprotic organic solvents such as N,N-dimethylformamide and dimethyl sulfoxide can be used. The polymerization solvents may be used alone or in combination of two or more of the polymerization solvents.

A concentration of the monomer (total concentration of hydrophilic and hydrophobic monomers) in the polymerization solvent can be, for example, preferably 3% by mass to 90% by mass, more preferably 5% by mass to 80% by mass, and particularly preferably 8% by mass to 50% by mass.

In the polymerization, polymerization conditions are also not particularly limited as long as the copolymerization proceeds. For example, a polymerization temperature can be, for example, preferably 30° C. to 150° C., more preferably 40° C. to 100° C., and a polymerization time can be, for example, preferably 30 minutes to 30 hours, more preferably 3 hours to 24 hours.

Further, in copolymerization, chain transfer agents, polymerization rate adjusting agents, surfactants, water-soluble polymers, water-soluble inorganic compounds (alkali metal salts, alkali metal hydroxides, polyvalent metal salts, non-reducing alkali metal salt, pH buffers, and the like), inorganic acids, inorganic acid salts, organic acids, organic acid salts, and other additives may be appropriately used, if necessary.

The block copolymer after the copolymerization is preferably purified by a general purification method such as a reprecipitation method, a dialysis method, an ultrafiltration method, or an extraction method.

Other Components

The surface lubricating layer may contain other components in addition to the block copolymer. The other components are not particularly limited, and when the medical instrument is intended to be inserted into a body cavity or a lumen such as a catheter, examples of the other components can include drugs (physiologically active substances) such as anticancer agents, immunosuppressive agents, antibiotics, anti-rheumatic drugs, antithrombotic drugs, HMG-CoA reductase inhibitors, ACE inhibitors, calcium antagonists, antihyperlipidemic drugs, integrin inhibitors, antiallergic agents, antioxidants, GPIIb/IIIa antagonists, retinoids, flavonoids, carotinoids, lipid improving drugs, DNA synthesis inhibitors, tyrosine kinase inhibitors, antiplatelet agents, vascular smooth muscle proliferation inhibitors, anti-inflammatory drugs, bio-derived materials, interferons, and NO production promoting materials. Here, an addition amount of other components is not particularly limited, and the amount is the same as the amount usually used. Finally, the addition amount of the other components is appropriately selected in consideration of severity of a disease to be applied, a weight of a patient, and the like.

Method for Forming Surface Lubricating Layer

A method for forming the surface lubricating layer according to the present disclosure is not particularly limited, and the method preferably includes coating the base with a solution containing the block copolymer having the structural unit (A) derived from the hydrophobic monomer and the structural unit (B) derived from the hydrophilic monomer, and a solvent ((II-a) solution coating step, coating layer forming step), and drying the coating layer ((II-b) drying step).

(II-a) Solution Coating Step (Coating Layer Forming Step)

In the method for forming the surface lubricating layer according to the present disclosure, first, the intermediate layer is coated with the solution (also referred to as "coating solution for the surface lubricating layer" in the present description) containing the block copolymer and the solvent ((II-a) solution coating step, coating layer forming step). The solution coating step is performed for the purpose of supporting (or covering) the surface lubricating layer containing the block copolymer on the upper part of the intermediate layer. The expression "supporting" means a state where the surface lubricating layer is immobilized so as not to be easily released from a surface of the intermediate layer, and includes not only a form in which the entire surface of the intermediate layer is completely covered by the surface lubricating layer, but also a form in which only a part of the surface of the intermediate layer is covered by the surface lubricating layer, that is, a form in which the surface lubricating layer is attached only to a part of the surface of the intermediate layer. Therefore, the coating method with the solution is not particularly limited as long as the solution containing the block copolymer having the structural unit (A) and the structural unit (B) and the solvent is used, and a method same as a known method or an appropriate modification of a known method can be applied.

In the solution coating step, specifically, the block copolymer is dissolved in the solvent to prepare the block copolymer solution (coating solution for the surface lubricating layer), and the intermediate layer is coated with the solution (coating solution) to form a coating layer.

The solvent used for dissolving the block copolymer according to the present disclosure is not particularly limited as long as the solvent can dissolve the block copolymer according to the present disclosure. Specific examples of the solvent can include water, alcohols such as methanol, ethanol, isopropanol, and ethylene glycol, ketones such as acetone, methyl ethyl ketone, and cyclohexanone, esters such as ethyl acetate, halides such as chloroform, olefins such as hexane, ethers such as tetrahydrofuran (THF) and butyl ether, aromatics such as benzene and toluene, amides such as N,N-dimethylformamide (DMF), and sulfoxides such as dimethyl sulfoxide, but the solvent is not limited to the disclosed solvents. The solvents may be used alone or in combination of two or more of the solvents. Among the solvents, from the viewpoints that the block copolymer can be uniformly dissolved and the coating solution can be uniformly applied, the solvent of the coating solution is preferably ketones such as acetone and amides such as DMF, and particularly preferably acetone and DMF.

Preparation of Block Copolymer Solution (Coating Solution for Surface Lubricating Layer)

The block copolymer solution (coating solution for the surface lubricating layer) is prepared using the block copolymer and the solvent. An order and a method of adding the above components are not particularly limited. The above components may be added collectively or separately, stepwise or continuously. In addition, a mixing method is not particularly limited, and a known method can be used. A preferred method for preparing the block copolymer solution (coating solution) includes sequentially adding the block copolymer to the solvent and stirring the copolymer in the solvent.

A concentration of the block copolymer in the block copolymer solution (coating solution for the surface lubricating layer) is not particularly limited. From the viewpoint of improving a coating property, a lubricating property, and durability of the surface lubricating layer, the concentration of the block copolymer in the solution (coating solution) can be, for example, preferably 0.01% by mass to 20% by mass, more preferably 0.05% by mass to 15% by mass, and still more preferably 1% by mass or more and less than 15% by mass. When the concentration of the block copolymer is in the above range, the lubricating property and the durability of the surface lubricating layer may be sufficiently exhibited. In addition, a uniform surface lubricating layer with a desired thickness can be easily obtained with a single coating, and the viscosity of the solution is within an appropriate range, which is preferable in terms of operability (for example, ease of coating) and production efficiency. However, even when the concentration deviates from the above range, the surface lubricating layer can be sufficiently used as long as the functions and effects of the present disclosure are not influenced.

Coating with Block Copolymer Solution (Coating Solution for Surface Lubricating Layer)

Next, after preparing the solution (coating solution for the surface lubricating layer) containing the block copolymer and the solvent as described above, the intermediate layer is coated with the solution.

A method of coating the surface of the intermediate layer with the block copolymer solution (coating solution for surface lubricating layer) is not particularly limited, and known methods in the related art such as a coating and printing method, an immersion method (dipping method, dip coating method), a spraying method (spray method), a spin coating method, a mixed solution impregnated sponge coating method, a bar coating method, a die coating method, a reverse coating method, a comma coating method, a gravure coating method, and a doctor knife method can be applied.

When the surface lubricating layer is to be formed on a thin and narrow inner surface of a catheter, an injection needle, or the like, the base on which the intermediate layer is formed may be immersed in the coating solution, and defoaming is performed while reducing a pressure in the system. By performing defoaming while reducing the pressure, the solution can be quickly permeated into the thin and narrow inner surface and formation of the surface lubricating layer can be promoted.

When the surface lubricating layer is to be formed only on a part of the intermediate layer, by immersing only the part of the base on which the intermediate layer is formed in the coating solution to coat the part of the intermediate layer with the coating solution, the surface lubricating layer can be formed on a desired surface portion of the intermediate layer.

When it is difficult to immerse only the part of the base on which the intermediate layer is formed in the coating solution, upon protecting (cover, and the like) in advance, with an appropriate member or material that can be attached and detached (mounted and dismounted), a surface portion of the intermediate layer where the surface lubricating layer is not required to be formed, the base on which the intermediate layer is formed is immersed in the coating solution to coat the intermediate layer with the coating solution, then the protective member (material) on the surface portion of the intermediate layer where the surface lubricating layer is not required to be formed is removed, and then a drying treatment or the like is performed, thereby forming the surface lubricating layer on the desired surface portion of the intermediate layer. However, the present disclosure is not limited to these forming methods, and the surface lubricating layer can be formed by appropriately using known methods. For example, when it is difficult to immerse only the part of the intermediate layer in the coating solution, another coating method (for example, a method of coating a predetermined surface portion of a medical instrument with a coating solution by using a coating device such as a spray device, a bar coater, a die coater, a reverse coater, a comma coater, a gravure coater, a spray coater, and a doctor knife) may be applied instead of the immersion method. When a structure of the medical instrument is required to include a surface lubricating layer in both an outer surface and an inner surface of a cylindrical tool of the medical instrument, the immersion method (dipping method) is preferably used because both the outer surface and the inner surface can be coated at one time.

A coating amount of the block copolymer solution (coating solution for the surface lubricating layer) is preferably such that a thickness of the obtained coating film (surface lubricating layer) can be, for example, 0.1 μm to 10 μm, more preferably 0.5 μm to 5 μm, and still more preferably 1 μm to 3 μm. Within such a range, even when the surface lubricating layer is swollen by a body fluid, an influence on an outer shape of the medical instrument due to an increase in film thickness of the surface lubricating layer can be reduced. In particular, if the coating amount is such that the thickness of the coating film (surface lubricating layer) is 10 μm or less, it is possible to improve vascular insertability of medical instruments such as microcatheter that are to be inserted into small blood vessels.

(II-b) Drying Step

In the method for forming the surface lubricating layer according to the present disclosure, it is preferable to perform a drying step after coating the intermediate layer with the coating solution for the surface lubricating layer to form the coating layer.

A drying temperature is not particularly limited, and can be, for example, preferably 10° C. to 200° C., and more preferably 25° C. to 150° C. A drying time is not particularly limited, and can be, for example, preferably 30 minutes to 30 hours, and more preferably 1 hour to 25 hours.

A pressure condition during drying is not limited, and the drying step may be performed under a normal pressure (atmospheric pressure), or under a pressure or a reduced pressure. As a drying device, for example, a drying oven, an oven, a vacuum dryer, or the like can be used.

Use of Medical Instrument

The medical instrument according to the present disclosure is a device to be used in contact with a body fluid, blood, or the like, the surface of the medical instrument has a lubricating property in water-based liquids such as body fluids and physiological saline, and it is possible to improve operability and reduce damage to tissue mucous membranes. Examples of the medical instrument can include a catheter, a guide wire, and an indwelling needle to be used in blood vessels, and the following medical instruments are also shown.

(a) Catheters to be orally or nasally inserted or allowed to indwell in digestive organs such as stomach tube catheters, feeding catheters, and tubes for tubal feeding.

(b) Catheters to be orally or nasally inserted or allowed to indwell in a respiratory tract or trachea such as oxygen catheters, oxygen cannulas, tubes or cuffs for tracheal tubes, tubes or cuffs for tracheostomy tube, and tracheal aspiration catheters.

(c) Catheters to be inserted into or allowed to indwell in a urethra or ureter, such as urethra catheters, urinary catheters, and catheters and balloons of urethra balloon catheters.

(d) Catheters to be inserted or allowed to indwell in various lumens in a living body, organs and tissues, such as suction catheters, drain catheters, and rectal catheters.

(e) Catheters to be inserted or allowed to indwell in a blood vessel, such as indwelling needles, IVH catheters, thermodilution catheters, angiographic catheters, and vasodilatation catheters, and dilators or introducers, or guide wires, stylets, and the like for these catheters.

(f) Artificial tracheae, artificial bronchial tubes, and the like.

(g) Medical instruments for extracorporeal circulation therapy (artificial lungs, artificial hearts, artificial kidneys, and the like) and circuits for the medical instruments.

The medical instrument according to the present disclosure is preferably a catheter.

EXAMPLES

Effects of the present disclosure will be described with reference to the following Examples and Comparative Examples. However, the technical scope of the present disclosure is not limited to the following Examples. In the following Examples, unless otherwise specified, the operation was performed at room temperature (25° C.). Unless otherwise specified, "%" and "parts" mean "% by mass" and "parts by mass", respectively.

Preparation of (Meth)Acrylic Acid-Modified Polyester Resin

A (meth)acrylic-modified polyester resin 1 (weight average molecular weight: 10,000 or more, hereinafter simply referred to as "polyester resin 1") containing the following compositions was prepared:

Polyester resin segment

Polycarboxylic acid component: content of terephthalic acid: 19 mol % content of isophthalic acid: 6 mol %

Polyhydric alcohol component: content: 25 mol %

Monomer used diethylene glycol:ethylene glycol:neopentyl glycol=11.8:10.3:2.9 (molar ratio)

(Meth)acrylic resin segment (meth)acrylic modification ratio: 50 mol %

Monomer used methyl methacrylate:n-butyl acrylate:glycidyl methacrylate:methacrylic acid=27.0:13.5:5.5:4.0 (molar ratio)

Bireactive monomer methacrylic acid amount used: 4.0 mol % based on the total number of moles of the monomers constituting the (meth)acrylic-modified polyester resin.

Similarly, (meth)acrylic-modified polyester resins 2 to 10 (hereafter, also simply referred to as "polyester resins 2 to 10") having (meth)acrylic modification ratios, contents of terephthalic acid, contents of isophthalic acid, and contents of polyhydric alcohol component in Table 1 (FIG. 3), and an unmodified polyester resin 11 not subjected to (meth)acrylic modification were prepared.

Types and amounts of the bireactive monomer used, types of monomers used in the polyhydric alcohol component and the (meth)acrylic resin segment, molar ratio of monomers used in the polyhydric alcohol component, and molar ratio of monomers used in the (meth)acrylic resin segment are common to the polyester resins 1 to 10 and the unmodified polyester resin 11. Weight average molecular weights of the polyester resins 1 to 10 and the unmodified polyester resin 11 were all 10,000 or more.

Preparation of Polyurethane Resin

F-2170D (weight average molecular weight: 10,000 or more) manufactured by DKS Co., Ltd. was prepared.

Preparation of Block Copolymer

A diblock copolymer (structural unit (A):structural unit (B)=1/12 (molar ratio)) containing glycidyl methacrylate (GMA)/N,N-dimethylacrylamide (DMAA)=1/12 (molar ratio) was prepared.

Example 1

Sample Preparation (Formation of Intermediate Layer)

A resin component was dissolved in a 1-propanol aqueous solution (water/1-propanol=40/60 (mass ratio)) (stirring time: 1 minute) such that a mass ratio of the polyester resin 1 to the polyurethane resin was 70/30 and a total solid concentration of the resin component was 3% by mass to prepare a coating solution for an intermediate layer. Next, in an environment with a temperature of 25° C. and a relative humidity of 45% RH, a polyester tube (Pelprene®) P420H manufactured by Toyobo Co., Ltd., outer diameter: 0.9 mm×length: 600 mm) was immersed in the coating solution for the intermediate layer, pulled up at a speed of 15 mm/sec, and the tube was coated with the coating solution for the intermediate layer. Thereafter, the tube was dried in a drying oven kept at 100° C. for 10 minutes to obtain a tube 1-1 on which an intermediate layer (dry film thickness: 150 nm) was laminated.

Sample Preparation (Formation of Surface Lubricating Layer)

The block copolymer was dissolved in acetone (stirring time: 10 minutes) such that the concentration of the block copolymer was 5% by mass, and a coating solution for a surface lubricating layer was prepared. Next, in an environment with a temperature of 25° C. and a relative humidity of 45% RH, the tube 1-1 on which the intermediate layer was laminated was immersed in the coating solution for the surface lubricating layer, pulled up at a speed of 15 mm/sec, and the tube 1-1 was coated with the coating solution for the surface lubricating layer. Thereafter, the coated tube was dried in a drying oven kept at 100° C. for 2 hours to obtain a tube 1-2 on which the intermediate layer and the surface lubricating layer (dry film thickness: 1.5 μm) were laminated.

Example 2

A tube 2-1 on which an intermediate layer was laminated and a tube 2-2 on which an intermediate layer and a surface lubricating layer were laminated were obtained in the same manner as in Example 1 except that the mass ratio of the polyester resin 1 to the polyurethane resin was set to 50/50.

Example 3

A tube 3-1 on which an intermediate layer was laminated and a tube 3-2 on which an intermediate layer and a surface lubricating layer were laminated were obtained in the same manner as in Example 1 except that the mass ratio of the polyester resin 1 to the polyurethane resin was set to 30/70.

Example 4

A tube 4-1 on which an intermediate layer was laminated and a tube 4-2 on which an intermediate layer and a surface lubricating layer were laminated were obtained in the same manner as in Example 2 except that the polyester resin 2 was used instead of the polyester resin 1.

Example 5

A tube 5-1 on which an intermediate layer was laminated and a tube 5-2 on which an intermediate layer and a surface lubricating layer were laminated were obtained in the same manner as in Example 2 except that the polyester resin 3 was used instead of the polyester resin 1.

Example 6

A tube 6-1 on which an intermediate layer was laminated and a tube 6-2 on which an intermediate layer and a surface lubricating layer were laminated were obtained in the same manner as in Example 2 except that the polyester resin 4 was used instead of the polyester resin 1.

Example 7

A tube 7-1 on which an intermediate layer was laminated and a tube 7-2 on which an intermediate layer and a surface lubricating layer were laminated were obtained in the same manner as in Example 2 except that the polyester resin 5 was used instead of the polyester resin 1.

Example 8

A tube 8-1 on which an intermediate layer was laminated and a tube 8-2 on which an intermediate layer and a surface lubricating layer were laminated were obtained in the same manner as in Example 2 except that the polyester resin 6 was used instead of the polyester resin 1.

Example 9

A tube 9-1 on which an intermediate layer was laminated and a tube 9-2 on which an intermediate layer and a surface lubricating layer were laminated were obtained in the same manner as in Example 2 except that the polyester resin 7 was used instead of the polyester resin 1.

Example 10

A tube 10-1 on which an intermediate layer was laminated and a tube 10-2 on which an intermediate layer and a surface lubricating layer were laminated were obtained in the same manner as in Example 2 except that the polyester resin 8 was used instead of the polyester resin 1.

Example 11

A tube 11-1 on which an intermediate layer was laminated and a tube 11-2 on which an intermediate layer and a surface lubricating layer were laminated were obtained in the same manner as in Example 2 except that the polyester resin 9 was used instead of the polyester resin 1.

Example 12

A tube 12-1 on which an intermediate layer was laminated and a tube 12-2 on which an intermediate layer and a surface lubricating layer were laminated were obtained in the same manner as in Example 2 except that the polyester resin 10 was used instead of the polyester resin 1.

Comparative Example 1

A tube 13-1 on which an intermediate layer was laminated and a tube 13-2 on which an intermediate layer and a surface lubricating layer were laminated were obtained in the same manner as in Example 1 except that the polyurethane resin was not used.

Comparative Example 2

A tube 14-1 on which an intermediate layer was laminated and a tube 14-2 on which an intermediate layer and a surface lubricating layer were laminated were obtained in the same manner as in Example 1 except that the polyester resin 1 was not used.

Comparative Example 3

A tube 15-1 on which an intermediate layer was laminated and a tube 15-2 on which an intermediate layer and a surface lubricating layer were laminated were obtained in the same manner as in Example 2 except that Vylonal® MD-2000 (manufactured by Toyobo Co., Ltd., (meth)acrylic modification ratio: 0%, a sulfonic acid group-containing polyester resin, water-dispersed type) was used instead of the polyester resin 1.

Comparative Example 4

A tube 16-1 on which an intermediate layer was laminated and a tube 16-2 on which an intermediate layer and a surface lubricating layer were laminated were obtained in the same manner as in Example 2 except that Elitel® KT-8803 (manufactured by Unitika Ltd., (meth)acrylic modification ratio: 0%, a carboxy group-containing polyester resin, water-dispersed type) was used instead of the polyester resin 1.

Comparative Example 5

A tube 17-1 on which an intermediate layer was laminated and a tube 17-2 on which an intermediate layer and a surface lubricating layer were laminated were obtained in the same manner as in Example 2 except that the unmodified polyester resin 11 was used instead of the polyester resin 1.

Evaluation

Coefficient of Kinetic Friction

For the tubes 1-2 to 17-2 on which the intermediate layer and the surface lubricating layer were laminated, a coefficient of kinetic friction was evaluated using a friction measuring device (Handy Tribomaster TL201Ts manufactured by Trinity Lab Inc.) 20 shown in FIG. 1 according to the following method.

That is, a core material 18 was inserted into a tube 16 and a tube sample for evaluation (outer diameter: 0.9 mm×length: 200 mm) was prepared. The tube sample was laid down in a length direction, fixed to a petri dish 12, and immersed in ion-exchanged water having a height at which the entire tube sample was immersed. The petri dish 12 was placed on a moving table 15 of the friction measuring device 20 shown in FIG. 1. A terminal (diameter: 10 mm) 13 made of a hydrogenated styrene-based thermoplastic elastomer (SEBS) was brought into contact with the tube sample, and a load 14 of 200 g was applied onto the terminal. The coefficient of kinetic friction (unit: μN) when the moving table 15 was reciprocated 100 times horizontally was measured under a sliding distance of 20 mm and a sliding speed of 16.7 mm/sec.

Confirmation of Coating Film on Intermediate Layer

Leucomalachite green (manufactured by FUJIFILM Wako Pure Chemical Corporation) was dissolved in ion-exchanged water such that the concentration was 1% by mass to prepare a staining solution A. Next, a test same as in the above Coefficient of Kinetic Friction was performed on the tubes 1-1 to 17-1 on which the intermediate layer was laminated, which were prepared in the above Sample Preparation (Formation of Intermediate Layer), and the tube (outer diameter: 0.9 mm×length: 200 mm) for which the test was completed was immersed in the staining solution A for 30 minutes. Thereafter, the surface of the tube was washed with ion-exchanged water, the entire outer surface of the tube after washing with ion-exchanged water was visually confirmed, and a degree of staining was evaluated according to the following criteria. A spot where the staining is seen indicates a part where the base is exposed. That is, it is shown that the smaller the number of spots where the staining is seen, the better the adhesion between the base and the intermediate layer. A and B in the following evaluation are practical. A: no staining is seen on the entire outer surface of the tube B: 10% or more and less than 30% of the entire outer surface of the tube is stained
    C: 30% or more and less than 50% of the entire outer surface of the tube is stained
    D: 50% or more of the entire outer surface of the tube is stained.

Confirmation of Coating Film on Surface Lubricating Layer

Congo red (manufactured by FUJIFILM Wako Pure Chemical Corporation) was dissolved in ion-exchanged water such that the concentration was 1% by mass to prepare a staining solution B. Next, the test in the above Coefficient of Kinetic Friction was performed on the tubes 1-2 to 17-2 on which the intermediate layer and the surface lubricating layer were laminated, which were prepared in the above Sample Preparation (Formation of Surface Lubricating Layer), and the tube (outer diameter: 0.9 mm×length: 200 mm) for which the test was completed was immersed in the staining solution B for 30 minutes. Thereafter, the surface of the tube was washed with ion-exchanged water, the entire outer surface of the tube after washing with ion-exchanged water was visually confirmed, and a degree of staining was evaluated according to the following criteria. A spot where the staining is seen indicates the presence (covering) of the block copolymer. That is, it is shown that the more the spots where the staining is seen, the better the adhesion between the intermediate layer and the surface lubricating layer. A and B in the following evaluation are practical. A: the unstained portion of the entire outer surface of the tube is less than 5%

B: the unstained portion of the entire outer surface of the tube is 5% or more and 10% or less C: the unstained portion of the entire outer surface of the tube is more than 10% and 30% or less D: the unstained portion of the entire outer surface of the tube is more than 30%.

Table 2 (FIG. 4) shows evaluation results of the coefficient of kinetic friction, the confirmation of the coating film on the intermediate layer, and the confirmation of the coating film on the surface lubricating layer, as well as the composition of the (meth)acrylic-modified polyester resin and the composition of the intermediate layer.

As shown in Table 2, it was found that the tubes of Examples 1 to 12 were excellent in adhesion between the base and the intermediate layer, adhesion between the intermediate layer and the surface lubricating layer, and durability of the surface lubricating layer.

The following evaluations were performed using the obtained tubes 1-1 to 3-1 and the tubes 13-1 and 14-1 on which the intermediate layer was formed respectively in the same manner as in Examples 1 to 3 and Comparative Examples 1 and 2, and catheter tubes 1 to 3 and comparative catheter tubes 1 and 2 in which an intermediate layer and a surface lubricating layer were formed.

Elastic Modulus of Intermediate Layer

The tubes 1-1 to 3-1 and the tubes 13-1 and 14-1 on which the intermediate layer was laminated, which were prepared in the above Sample preparation (Formation of Intermediate Layer), were each cut into 10 mm. Next, the sample was placed in a scanning probe microscope (AFM5200S, manufactured by Hitachi High-Tech Science Corporation), a force mapping measurement was performed in a field of view of 500 nm×500 nm using a cantilever probe (SI-DF3P2, manufactured by Hitachi High-Tech Science Corporation), and the elastic modulus of the intermediate layer laminated on a tube surface was calculated. The elastic modulus was calculated by fitting an indentation-load curve obtained in the measurement to a theoretical curve obtained from a spring constant and a radius of curvature peculiar to the cantilever probe.

In this evaluation, the cantilever probe had a spring elastic modulus of 3.2 N/m, and a radius of curvature of a distal end shape of the probe was 4.68 nm. A Poisson's ratio of the sample was set to 0.3.

Sliding Durability Test

Figure 2:
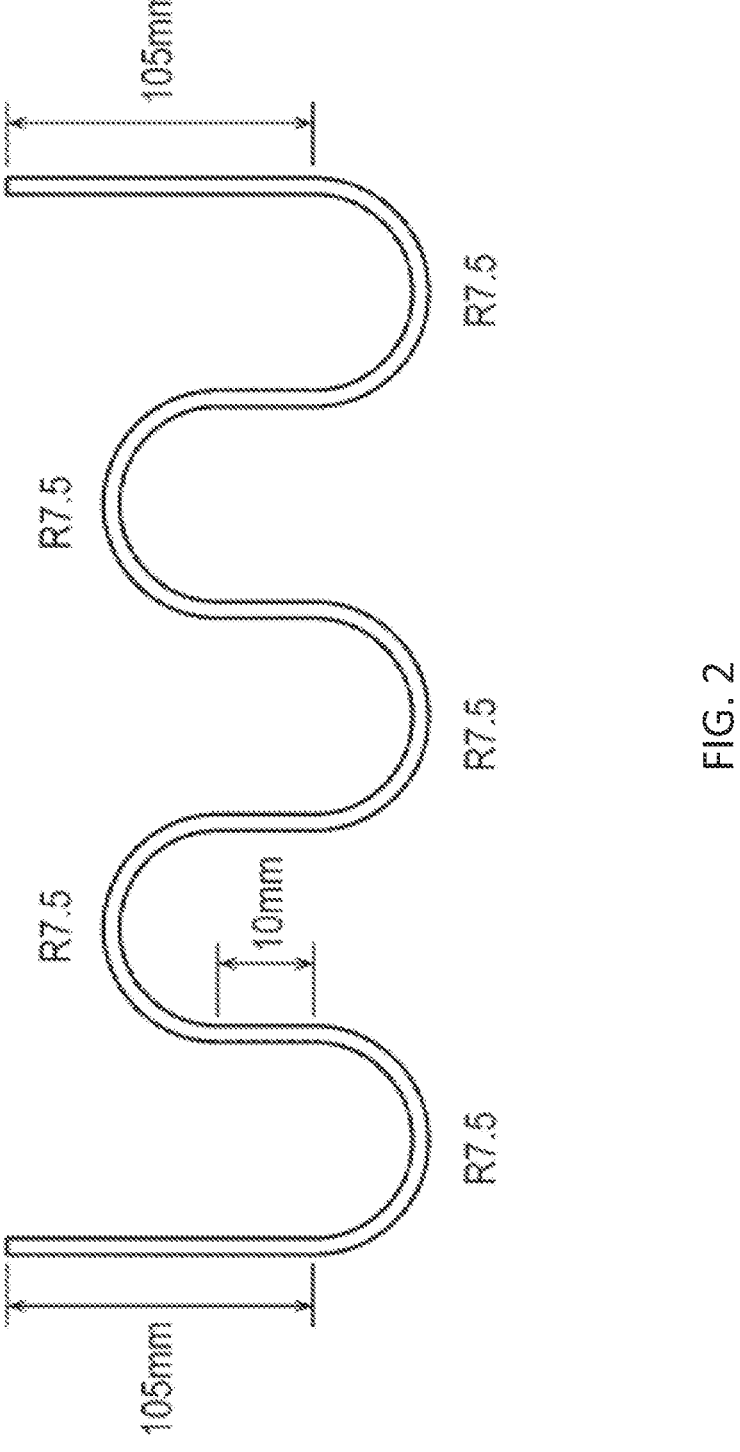
FIG. 2 is a schematic view of a tube used in a sliding durability test.

A bent tube made of polytetrafluoroethylene (PTFE) having an inner diameter of 1 mm filled with ion-exchanged water as shown in FIG. 2 was prepared, and a guide wire was inserted into the tube. As shown in FIG. 2, the tube has a total length of 370 mm and is provided with five bent portions each having a radius of curvature (R) of 7.5 mm in a wavy line. The bent portion was formed by bending a straight portion of 24 mm so as to have a radius of curvature of 7.5 mm.

Separately, a catheter tube (Progreat®) 2.7 Fr. before applying hydrophilic coating, manufactured by Terumo Corporation) was prepared, and in the procedure same as in Sample preparation (Formation of Intermediate Layer) and Sample preparation (Formation of Surface Lubricating Layer) in Examples 1 to 3 and Comparative Examples 1 and 2, the intermediate layer and the surface lubricating layer were laminated in a region 70 cm from a distal end to prepare the catheter tubes 1 to 3 and the comparative catheter tubes 1 and 2.

These catheter tubes were fitted into the guide wire inserted into the bent tube. At this time, the guide wire and the distal end of the catheter tube were inserted to an outlet of the bent tube made of PTFE. Thus, after each catheter tube was inserted into the guide wire in the bent tube made of PTFE for 50 reciprocations at a moving distance of 40 mm and an insertion speed of 500 mm/min, a maximum resistance value at this time was measured with a tensile tester (AG-10N, manufactured by Shimadzu Corporation). Based on the obtained maximum resistance value of the first reciprocation and the maximum resistance value of the 50th reciprocation, a sliding resistance increase rate was calculated using the following equation $$\text{Sliding resistance increase rate (\%)} = \{(\text{maximum resistance value of 50th reciprocation} - \text{maximum resistance value of first reciprocation}) / \text{maximum resistance value of first reciprocation}\} \times 100 \qquad \text{Math. 1}$$

Based on the calculated sliding resistance increase rate, the sliding durability of the catheter tube was evaluated according to the following criteria. A is practical. A: sliding resistance increase rate is 0% or more and less than 30%

B: sliding resistance increase rate is 30% or more.

Evaluation results of the elastic modulus and the sliding resistance increase rate are shown in Table 3 (FIG. 5).

As shown in Table 3, the catheter tubes of Examples 13 to 15 had an excellent balance between the elastic modulus (flexibility) and the sliding durability. Comparative Example 6 is a catheter tube on which the intermediate layer contains only the (meth)acrylic-modified polyester resin, and both flexibility and sliding durability are low. Comparative Example 7 is a catheter tube on which the intermediate layer contains only the polyurethane resin, and although the tube has flexibility, the sliding durability is low.

The detailed description above describes embodiments of a medical instrument. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical instrument comprising:

a base whose surface is partially made of a polyester resin;

an intermediate layer formed on at least a part of the surface of the base and containing a (meth)acrylic-modified polyester resin and a polyurethane resin;

a surface lubricating layer formed on an upper part of the intermediate layer and containing a block copolymer having a structural unit (A) derived from a hydrophobic monomer and a structural unit (B) derived from a hydrophilic monomer;

wherein at least one of the hydrophobic monomer and the hydrophilic monomer has a (meth)acryloyl group, and wherein the (meth)acrylic-modified polyester resin contains terephthalic acid and isophthalic acid; and wherein a molar ratio of a structural unit derived from the terephthalic acid to a structural unit derived from the isophthalic acid is 1.5 or more and 4.5 or less.

2. The medical instrument according to claim 1, wherein a mass ratio of the (meth)acrylic-modified polyester resin to the polyurethane resin in the intermediate layer is (meth) acrylic-modified polyester resin/polyurethane resin is 70/30 to 30/70.

3. The medical instrument according to claim 1, wherein a (meth)acrylic modification ratio of the (meth)acrylic-modified polyester resin is between 10 mol % and 60 mol % based on a total number of moles of monomers constituting the (meth)acrylic-modified polyester resin.

4. The medical instrument according to claim 1, wherein a content of a structural unit derived from the terephthalic acid is 12.5 mol % to 40 mol % based on a total number of moles of monomers constituting a (meth)acrylic resin segment and monomers constituting a polyester resin segment.

5. The medical instrument according to claim 1, wherein the hydrophobic monomer contains at least one selected from the group consisting of glycidyl acrylate, glycidyl methacrylate, 3,4-epoxycyclohexylmethyl acrylate, 3,4-epoxycyclohexylmethyl methacrylate, and β-methylglycidyl methacrylate.

6. The medical instrument according to claim 1, wherein the hydrophilic monomer contains at least one selected from the group consisting of N,N-dimethylacrylamide, N,N-diethylacrylamide, acrylamide, 2-hydroxyethyl acrylate, and 2-hydroxyethyl methacrylate.

7. The medical instrument according to claim 1, wherein the medical instrument is a catheter.

8. A catheter comprising:
a surface that is partially made of a polyester resin;
an intermediate layer formed on at least a part of the surface and containing a (meth)acrylic-modified polyester resin and a polyurethane resin;
a surface lubricating layer formed on an upper part of the intermediate layer and containing a block copolymer having a structural unit derived from a hydrophobic monomer and a structural unit derived from a hydrophilic monomer;
at least one of the hydrophobic monomer and the hydrophilic monomer has a (meth)acryloyl group, and wherein the (meth)acrylic-modified polyester resin contains terephthalic acid and isophthalic acid, and a molar ratio of a structural unit derived from the terephthalic acid to a structural unit derived from the isophthalic acid is 1.5 or more and 4.5 or less; and
wherein the hydrophobic monomer contains at least one selected from the group consisting of glycidyl acrylate, glycidyl methacrylate, 3,4-epoxycyclohexylmethyl acrylate, 3,4-epoxycyclohexylmethyl methacrylate, and β-methylglycidyl methacrylate, and the hydrophilic monomer contains at least one selected from the group consisting of N,N-dimethylacrylamide, N,N-diethylacrylamide, acrylamide, 2-hydroxyethyl acrylate, and 2-hydroxyethyl methacrylate.

9. The catheter according to claim 8, wherein a mass ratio of the (meth)acrylic-modified polyester resin to the polyurethane resin in the intermediate layer is (meth)acrylic-modified polyester resin/polyurethane resin is 70/30 to 30/70.

10. The catheter according to claim 8, wherein a (meth) acrylic modification ratio of the (meth)acrylic-modified polyester resin is between 10 mol % and 60 mol % based on a total number of moles of monomers constituting the (meth)acrylic-modified polyester resin.

11. The catheter according to claim 8, wherein a content of a structural unit derived from the terephthalic acid is 12.5 mol % to 40 mol % based on a total number of moles of monomers constituting a (meth)acrylic resin segment and monomers constituting a polyester resin segment.

12. A method of coating a medical instrument, the method comprising:
applying an intermediate layer containing a (meth) acrylic-modified polyester resin and a polyurethane resin on at least a part of a surface of a base, the surface being partially made of a polyester resin, the (meth) acrylic-modified polyester resin containing terephthalic acid and isophthalic acid, and a molar ratio of a structural unit derived from the terephthalic acid to a structural unit derived from the isophthalic acid is 1.5 or more and 4.5 or less; and
applying a surface lubricating layer on an upper part of the intermediate layer, the surface lubricating layer containing a block copolymer having a structural unit derived from a hydrophobic monomer and a structural unit derived from a hydrophilic monomer, and wherein at least one of the hydrophobic monomer and the hydrophilic monomer has a (meth)acryloyl group.

13. The method according to claim 12, wherein a mass ratio of the (meth)acrylic-modified polyester resin to the polyurethane resin in the intermediate layer is (meth)acrylic-modified polyester resin/polyurethane resin is 70/30 to 30/70.

14. The method according to claim 12, wherein a (meth) acrylic modification ratio of the (meth)acrylic-modified polyester resin is between 10 mol % and 60 mol % based on a total number of moles of monomers constituting the (meth)acrylic-modified polyester resin.

* * * * *